US009788957B2

(12) United States Patent
Koka

(10) Patent No.: US 9,788,957 B2
(45) Date of Patent: Oct. 17, 2017

(54) GLENOID VAULT FIXATION

(71) Applicants: COORSTEK MEDICAL LLC, Providence, UT (US); Cleveland Clinic Foundation, Cleveland, OH (US)

(72) Inventor: Dinesh Koka, Orlando, FL (US)

(73) Assignees: Cleveland Clinic Foundation, Cleveland, OH (US); Coorstek Medical LLC, Providence, UT (US)

(*) Notice: Subject to any disclaimer, the term of this patent is extended or adjusted under 35 U.S.C. 154(b) by 368 days.

(21) Appl. No.: 14/205,755

(22) Filed: Mar. 12, 2014

(65) Prior Publication Data

US 2014/0194995 A1     Jul. 10, 2014

Related U.S. Application Data

(63) Continuation-in-part of application No. 13/708,799, filed on Dec. 7, 2012, now Pat. No. 9,414,927.
(Continued)

(51) Int. Cl.
*A61F 2/40* (2006.01)
*A61F 2/46* (2006.01)
(Continued)

(52) U.S. Cl.
CPC .......... *A61F 2/4081* (2013.01); *A61F 2/4637* (2013.01); *A61B 17/8052* (2013.01);
(Continued)

(58) Field of Classification Search
CPC ........ A61F 2/40; A61F 2/4081; A61F 2/4637; A61F 2/389; A61F 2002/30504;
(Continued)

(56) References Cited

U.S. PATENT DOCUMENTS

| 1,105,105 A | 7/1914 | Sherman |
| 2,580,821 A | 1/1952 | Nicola |

(Continued)

FOREIGN PATENT DOCUMENTS

| DE | 3630276 A1 | 3/1988 |
| DE | 10 2006 041551 A1 | 11/2007 |

(Continued)

OTHER PUBLICATIONS

International Preliminary Report on Patentability and Written Opinion for International Application No. PCT/US2012/024035, dated Jun. 10, 2014 (6 pages).
(Continued)

*Primary Examiner* — Brian Dukert
(74) *Attorney, Agent, or Firm* — Ramey & Schwaller, LLP; Craig Buschmann

(57) ABSTRACT

A system is provided which includes an articulating component, a post, a reception member and a bone engaging member. The articulating component includes an articulating surface and a second surface opposite the articulating surface. The post is disposed below the second surface. The reception member is configured to receive the post. The bone engaging member is configured to be embedded in a bone, wherein the bone engaging member is configured to receive the reception member. The reception member includes a reception member inside surface, wherein the reception member inside surface faces the post when the post is received by the reception member. A first portion of the reception member inside surface defines a tapered configuration and the reception member inside surface comprises at least one ratchet interface.

19 Claims, 19 Drawing Sheets

Related U.S. Application Data

(60) Provisional application No. 61/777,591, filed on Mar. 12, 2013.

(51) Int. Cl.
*A61F 2/30* (2006.01)
*A61B 17/86* (2006.01)
*A61B 17/80* (2006.01)

(52) U.S. Cl.
CPC .......... *A61B 17/86* (2013.01); *A61F 2/30749* (2013.01); *A61F 2002/305* (2013.01); *A61F 2002/3054* (2013.01); *A61F 2002/30367* (2013.01); *A61F 2002/30377* (2013.01); *A61F 2002/30387* (2013.01); *A61F 2002/30405* (2013.01); *A61F 2002/30774* (2013.01); *A61F 2002/30878* (2013.01); *A61F 2002/4085* (2013.01); *A61F 2002/4641* (2013.01); *A61F 2002/4681* (2013.01)

(58) Field of Classification Search
CPC ........ A61F 2002/305; A61F 2002/3054; A61F 2002/4641; A61F 2002/4085
See application file for complete search history.

(56) References Cited

U.S. PATENT DOCUMENTS

| | | | |
|---|---|---|---|
| 2,780,223 | A | 2/1957 | Haggland |
| 3,593,709 | A | 7/1971 | Halloran |
| 4,364,382 | A | 12/1982 | Mennen |
| 4,429,690 | A | 2/1984 | Angelino-Pievani |
| 5,047,058 | A | 9/1991 | Roberts et al. |
| 5,387,241 | A | 2/1995 | Hayes |
| 5,487,741 | A | 1/1996 | Maruyama et al. |
| 5,489,311 | A * | 2/1996 | Cipolletti ............... A61F 2/389 623/20.34 |
| 5,702,447 | A | 12/1997 | Walch et al. |
| 5,755,800 | A | 5/1998 | O'Neil et al. |
| 5,766,255 | A | 6/1998 | Slamin et al. |
| 5,984,969 | A | 11/1999 | Matthews et al. |
| 6,005,018 | A | 12/1999 | Cicierega et al. |
| 6,093,188 | A | 7/2000 | Murray |
| 6,200,321 | B1 | 3/2001 | Orbay et al. |
| 6,228,119 | B1 | 5/2001 | Ondrla et al. |
| 6,273,892 | B1 | 8/2001 | Orbay et al. |
| 6,306,172 | B1 * | 10/2001 | O'Neil ................. A61F 2/3868 623/20.15 |
| 6,364,881 | B1 | 4/2002 | Apgar et al. |
| 6,406,495 | B1 | 6/2002 | Schoch |
| 6,514,287 | B2 | 2/2003 | Ondrla et al. |
| 6,517,543 | B1 * | 2/2003 | Berrevoets ............ A61B 17/68 411/324 |
| 6,699,289 | B2 | 3/2004 | Iannotti et al. |
| 6,953,478 | B2 | 10/2005 | Bouttens et al. |
| 7,169,184 | B2 | 1/2007 | Dalla Pria |
| 7,204,854 | B2 | 4/2007 | Guederian et al. |
| 7,235,106 | B2 | 6/2007 | Daniels et al. |
| 7,329,284 | B2 | 2/2008 | Maroney et al. |
| 7,445,638 | B2 | 11/2008 | Beguin et al. |
| 7,604,665 | B2 | 10/2009 | Iannotti et al. |
| 7,608,109 | B2 | 10/2009 | Dalla Pria |
| 7,611,539 | B2 | 11/2009 | Bouttens et al. |
| 7,753,959 | B2 | 7/2010 | Berelsman et al. |
| 7,892,287 | B2 | 2/2011 | Deffenbaugh |
| 7,896,886 | B2 | 3/2011 | Orbay et al. |
| 7,922,769 | B2 | 4/2011 | Deffenbaugh et al. |
| 8,007,538 | B2 | 8/2011 | Gunther |
| 8,048,165 | B2 | 11/2011 | Isch et al. |
| 2004/0162619 | A1 | 8/2004 | Blaylock et al. |
| 2005/0049709 | A1 | 3/2005 | Tornier |
| 2005/0060039 | A1 | 3/2005 | Cyprien |
| 2005/0192578 | A1 | 9/2005 | Horst |
| 2005/0261775 | A1 | 11/2005 | Baum et al. |
| 2005/0278030 | A1 | 12/2005 | Tornier et al. |
| 2006/0074430 | A1 | 4/2006 | Deffenbaugh et al. |
| 2006/0200248 | A1 | 9/2006 | Beguin et al. |
| 2006/0235407 | A1 | 10/2006 | Wang et al. |
| 2006/0276905 | A1 | 12/2006 | Calamel |
| 2007/0021838 | A1 | 1/2007 | Dugas et al. |
| 2007/0038302 | A1 | 2/2007 | Shultz et al. |
| 2007/0055380 | A1 | 3/2007 | Berelsman et al. |
| 2007/0142917 | A1 | 6/2007 | Roche et al. |
| 2007/0156246 | A1 | 7/2007 | Meswania et al. |
| 2007/0179624 | A1 | 8/2007 | Stone et al. |
| 2007/0225817 | A1 | 9/2007 | Reubelt et al. |
| 2007/0244563 | A1 | 10/2007 | Roche et al. |
| 2007/0260321 | A1 | 11/2007 | Stchur |
| 2007/0270855 | A1 | 11/2007 | Partin |
| 2008/0015589 | A1 | 1/2008 | Hack |
| 2008/0109000 | A1 | 5/2008 | Maroney et al. |
| 2008/0208348 | A1 | 8/2008 | Fitz |
| 2008/0243191 | A1 | 10/2008 | Tipirneni et al. |
| 2009/0149961 | A1 | 6/2009 | Dallmann |
| 2009/0164021 | A1 | 6/2009 | Dallmann |
| 2009/0192621 | A1 | 7/2009 | Winslow et al. |
| 2009/0281630 | A1 | 11/2009 | Delince et al. |
| 2009/0292364 | A1 | 11/2009 | Linares |
| 2010/0069966 | A1 | 3/2010 | Castaneda et al. |
| 2010/0070044 | A1 | 3/2010 | Maroney et al. |
| 2010/0114326 | A1 | 5/2010 | Winslow et al. |
| 2010/0125336 | A1 | 5/2010 | Johnson et al. |
| 2010/0129138 | A1 | 5/2010 | Lariviere |
| 2010/0161065 | A1 | 6/2010 | Williams et al. |
| 2010/0161066 | A1 | 6/2010 | Iannotti et al. |
| 2010/0217328 | A1 | 8/2010 | Terrill et al. |
| 2010/0217399 | A1 | 8/2010 | Groh |
| 2010/0222886 | A1 | 9/2010 | Wiley et al. |
| 2010/0228352 | A1 | 9/2010 | Courtney, Jr. et al. |
| 2010/0274359 | A1 | 10/2010 | Brunnarius et al. |
| 2011/0060372 | A1 | 3/2011 | Allison |
| 2011/0106266 | A1 | 5/2011 | Schwyzer et al. |
| 2011/0112651 | A1 | 5/2011 | Blaylock et al. |
| 2011/0137424 | A1 | 6/2011 | Lappin et al. |
| 2011/0144758 | A1 | 6/2011 | Deffenbaugh |
| 2011/0152946 | A1 | 6/2011 | Frigg et al. |
| 2013/0090695 | A1 | 4/2013 | Bernstein et al. |

FOREIGN PATENT DOCUMENTS

| | | |
|---|---|---|
| EP | 0339530 A2 | 11/1989 |
| EP | 1488764 A1 | 12/2004 |
| EP | 1607067 A1 | 12/2005 |
| EP | 1656910 A1 | 5/2006 |
| EP | 1782764 A2 | 5/2007 |
| EP | 1980221 A1 | 10/2008 |
| FR | 2855743 A1 | 12/2004 |
| WO | WO 93/09733 A1 | 5/1993 |
| WO | WO 2007/134691 A1 | 11/2007 |
| WO | WO 2008/040408 A1 | 4/2008 |
| WO | WO 2009/092830 A1 | 7/2009 |
| WO | WO 2009/100310 A1 | 8/2009 |

OTHER PUBLICATIONS

International Preliminary Report on Patentability and Written Opinion for International Application No. PCT/US2012/068605, dated Jun. 10, 2014 (6 pages).
International Search Report for International Application No. PCT/US2012/024035, dated Aug. 7, 2012 (2 pages).
International Search Report for International Application No. PCT/US2012/068605, dated Mar. 20, 2013 (3 pages).
Patent Examination Report No. 1 for Australian Application No. 2012321087, dated Mar. 21, 2014 (3 pages).
Patent Examination Report No. 1 for Australian Application No. 2012321093, dated Feb. 26, 2014 (3 pages).
Patent Examination Report No. 2 for Australian Application No. 2012321093, dated Apr. 11, 2015 (3 pages).
Fucentese, Sandro; Total shoulder Arthroplasty with an Uncemented Soft-Metal-Backed Glenoid Component, Journal of shoulder elbow Surgery (2010) 19, 624-631.

(56) References Cited

OTHER PUBLICATIONS

Jones, Geary C.; In-Vitro Evaluation of ta Polyurethane Compliant LA, Proc. IMechE vol. 224 Part H: J. Engineering in Medicine (2010) pp. 551-563.

Kasten, P.; Mid-Term Survivorship Analysis of a shoulder Replacement with a Keeled Glenoid and a Modern Cementing Technique, Journal of Bone and Joint Surgery (BR) Mar. (2010) vol. 92-B, No. 387-392.

Sharma, Gulshan B.; Effect of Glenoid Prosthesis Design on Glenoid Bone Remodeling: Adaptive Finite Element based Simulation. Journal of Biomechanics 43(2010) 1653-1659.

Throckmorton, Thomas W.; Pegged Versus Keeled Glenoid Components in Total Shoulder Arthroplasty, Journal of Shoulder and Elbow Surgery (2010) 19, 726-733.

\* cited by examiner

GLENOID VAULT FIXATION

CROSS-REFERENCE TO RELATED APPLICATIONS

This application claims the benefit of and priority to:

U.S. Provisional Patent Application No. 61/777,591 filed Mar. 12, 2013, and is entitled GLENOID VAULT FIXATION; and U.S. patent application Ser. No. 13/708,799, filed Dec. 7, 2012, entitled SHOULDER ARTHROPLASTY, which is pending.

This application is also related to:

U.S. Provisional Patent Application No. 61/568,530, filed Dec. 8, 2011, entitled GLENOID VAULT FIXATION.

U.S. patent application Ser. No. 13/360,459, filed Jan. 27, 2012, entitled GLENOID VAULT FIXATION, which is pending.

P.C.T. Patent Application No. PCT/US2012/024035, filed Feb. 6, 2012, entitled GLENOID VAULT FIXATION, which is pending.

U.S. patent application Ser. No. 13/367,165, filed Feb. 6, 2012, entitled GLENOID VAULT FIXATION, which is pending.

U.S. Provisional Patent Application No. 61/604,391, filed Feb. 28, 2012, entitled GLENOID VAULT FIXATION.

U.S. Provisional Patent Application No. 61/615,560, filed Mar. 26, 2012, entitled GLENOID VAULT FIXATION.

U.S. Provisional Patent Application No. 61/701,484, filed Sep. 14, 2012, entitled GLENOID VAULT FIXATION.

P.C.T. Patent Application No. PCT/US2012/068605, filed Dec. 7, 2012, entitled SHOULDER ARTHROPLASTY, which is pending.

The above-referenced documents are hereby incorporated by reference in their entirety.

BACKGROUND

1. Technical Field

The present disclosure relates to shoulder repair and revision surgery. More specifically, but not exclusively, the present disclosure relates to systems and methods for glenoid and/or scapular restoration.

2. The Relevant Technology

One attribute of shoulder repair surgery is the limit of anatomical bone the patient has to provide for adequate repair and even more so with shoulder revision. The shoulder naturally only provides a limited amount of bone for the shoulder joint to function. When shoulder repair is needed it is often performed with large anchor devices embedded in what bone is available to allow for proper security of an articulating surface or glenosphere to attach to the anchor. These devices require a large removal of bone. Further revision surgery requires even greater bone loss as original anchors are removed and replaced with new anchors. There is a need to have the ability for revision shoulder repair without removal of the original anchors embedded in the bone.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION

The present invention relates to glenoid and/or scapular restoration. The systems and methods described herein may be readily adapted for other medical implants. The following description illustrates the principles of the invention, which may be applied in various ways to provide many different alternative embodiments. This description is not meant to limit the inventive concepts in the appended claims.

Standard medical planes of reference and descriptive terminology are employed in this specification. A sagittal plane divides a body into right and left portions. A midsagittal plane divides the body into equal right and left halves. A coronal plane divides a body into anterior and posterior portions. A transverse plane divides a body into superior and inferior portions. Anterior means toward the front of the body. Posterior means toward the back of the body. Superior means toward the head. Inferior means toward the feet. Medial means toward the midline of the body. Lateral means away from the midline of the body. Axial means toward a central axis of the body. Abaxial means away from a central axis of the body.

It may be necessary to exchange an articular component of a shoulder arthroplasty system during a revision procedure if, for example, the articular component shows signs of wear. In any revision procedure, it is desirable to minimize the revision disturbance to only those components or locations which require attention. If an entire glenoid construct must be removed in order to replace a worn articular surface, more damage may be done to the scapula, thus decreasing the likelihood for a successful outcome.

The present disclosure includes examples of connection mechanisms and methods to engage and disengage an articular component to an anchor assembly of a shoulder arthroplasty system. The articular component may be shaped like a natural glenoid articular surface and accompanying subchondral bone, or the articular component may be a glenosphere component according to a reverse shoulder design rationale. The articular component may even be a modular support component for further connection to an articular cap or insert. The anchor assembly may be described as a glenoid base or glenoid cup.

The connection mechanisms disclosed herein permit interchangeability of the articular component without disturbing the glenoid base.

Figure 1:
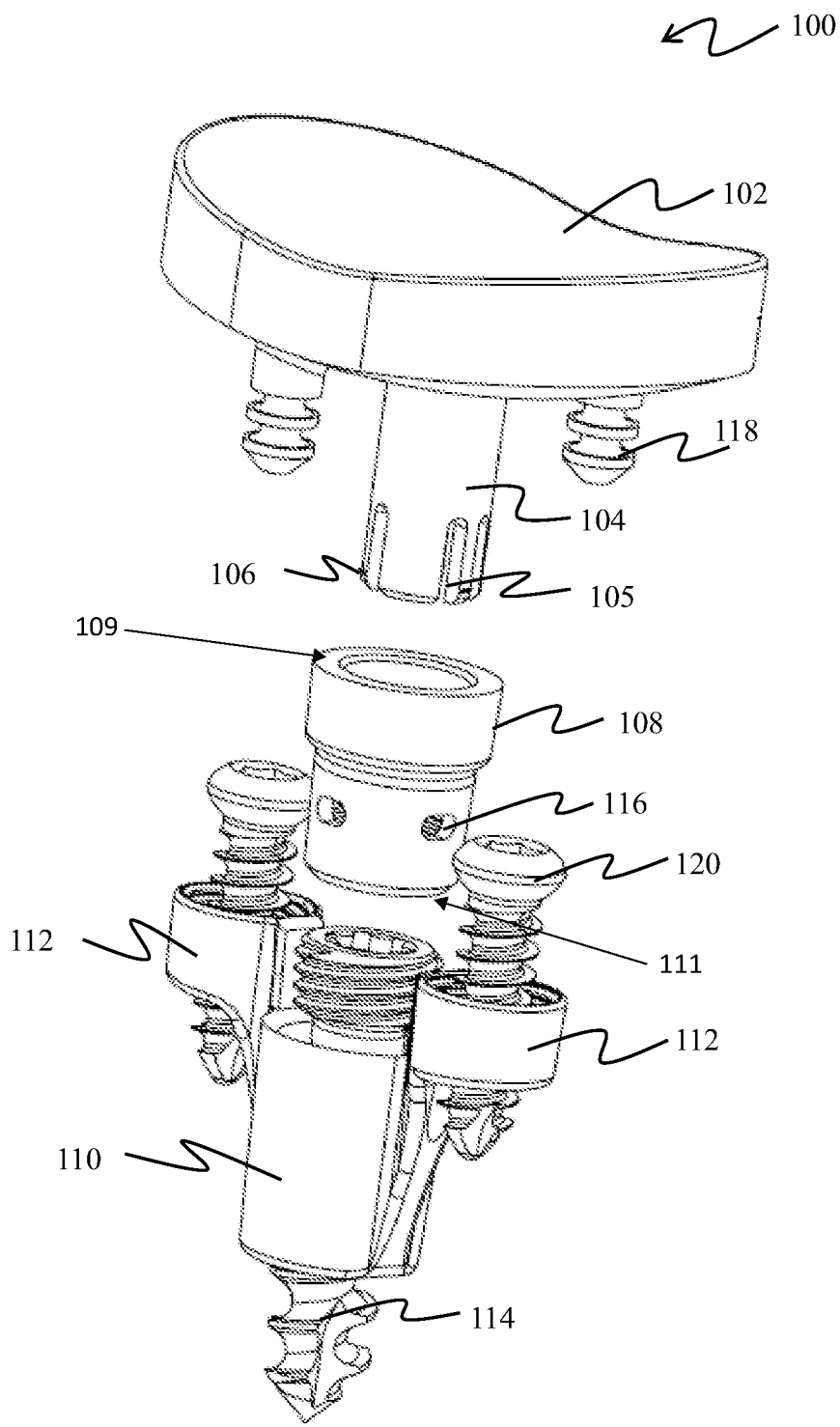
FIG. 1 is an exploded view of a system 100.

Referring to FIG. 1, a system 100 may be engaged with a glenoid. The system 100 may include an articulating component 102, a post or connecting means 104, a reception member 108 and a bone engaging member 110. The articulating component 102 may include pegs 118. The post 104 may include a ratchet interface 106. Further, the post 104 may comprise of at least one flexibility imparting means 105. The reception member 108 may define at least one installation-extraction slot 116. The reception member 108 may include a proximal end 109 and a distal end 111. The bone engaging member 110 may be engaged with the bone using screws 120 and an anchor 114.

The bone may be prepared to receive the bone engaging member 110. The anchor 114 and the screws 120 may be used to fasten the bone engaging member 110 to the bone. Upon engaging the bone engaging member 110 with the bone, the reception member 108 may be received in a bore provided in the bone engaging member 110. The reception member 108 receives the post 104. The articulating component 102 may be engaged with the post 104. The post 104 may be received by the reception member 108.

Figure 2A:
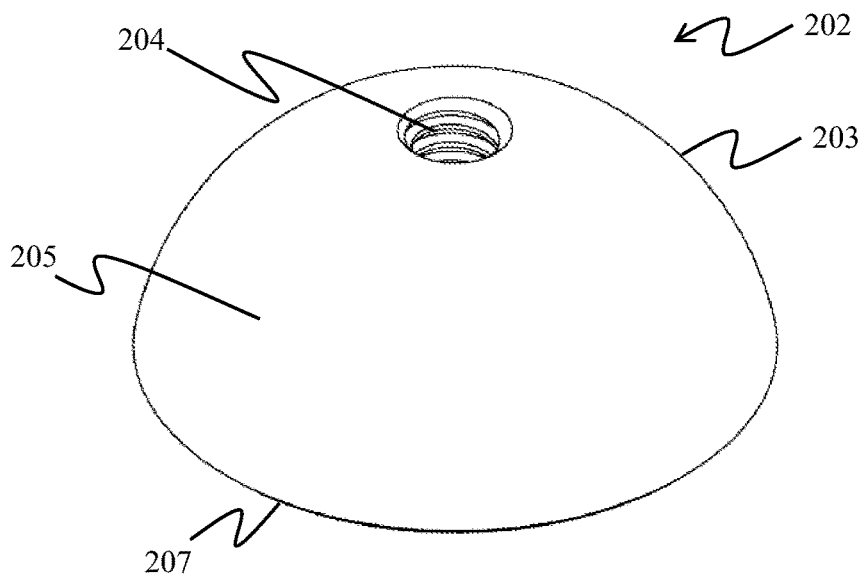
FIG. 2A is an isometric view of a glenosphere.
Figure 2B:
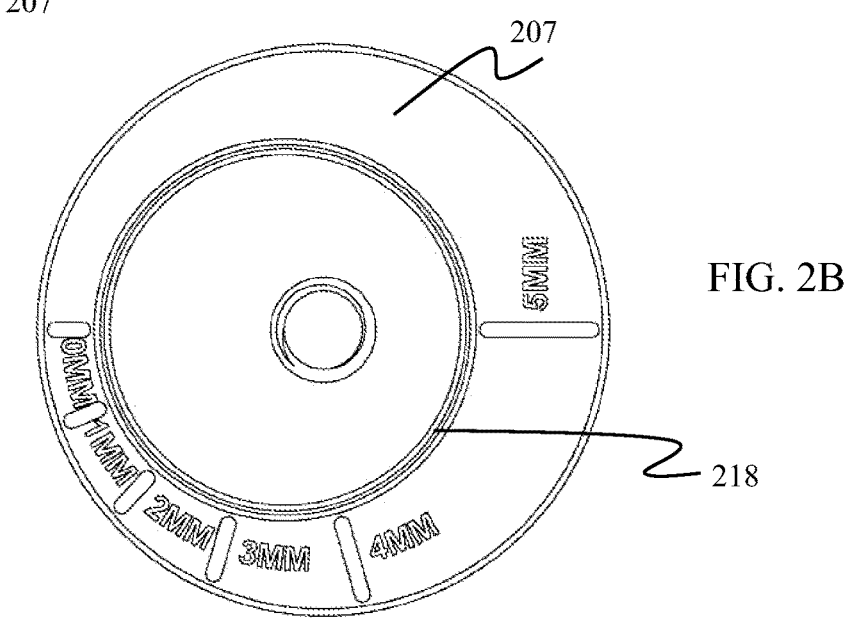
FIG. 2B is bottom view of the glenosphere of FIG. 2A.
Figure 2C:
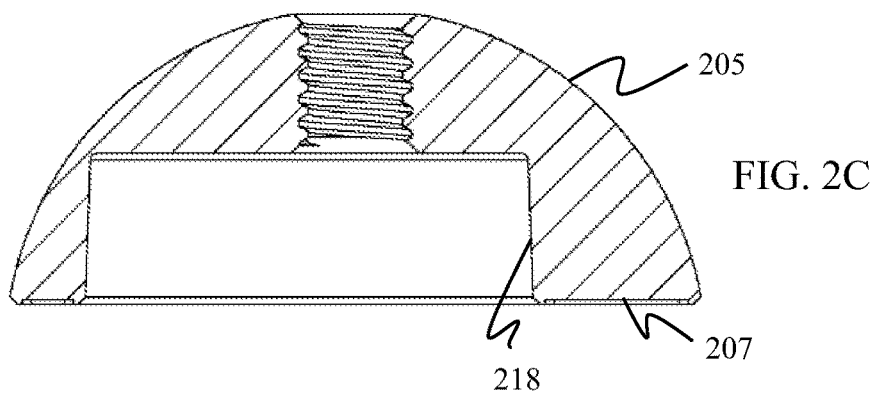
FIG. 2C is a cross-sectional view of glenosphere of FIG. 2A.

Referring to FIGS. 2A-2C, a glenosphere 202 may be a type of articulating component 102 which may replace or be used instead of the articulating component 102. The glenosphere 202 may be used for a reverse shoulder arthroplasty. The glenosphere 202 may include a body 203, an articulating surface 205 and a distal bone-facing surface 207. The distal bone facing surface 207 may also be referred to as second surface which is opposite to the articulating surface 205. The articulating surface 205 may be substantially semi-spherical or domed shape and may be smooth or rough on a micro or macro scale. The articulating surface 205 may also include an aperture 204 at or near the apex of the dome 205. The radius of curvature of the domed articulating surface 205 may vary to accommodate various patient anatomies.

The bone facing surface 207 may be substantially circular, and intersect the dome-shaped articulating surface 205 at all points along its circumference. The bone facing surface 207 may also include a substantially circular recessed portion 218 or dome cutout, which may be offset from the center of the bone facing surface 207. The recessed portion 218 may otherwise be oval or polygonal shaped. The recessed portion 218 may be shaped to receive a metaglene component 316 (illustrated in FIGS. 6A-6B). The aperture 204 may extend entirely from the articulating surface 205 to intersect the ceiling surface of the recessed portion. The aperture 204 may include a threaded portion to engage a threaded instrument that may be used for insertion or removal of the glenosphere that has been engaged with the bone.

Figure 3A:
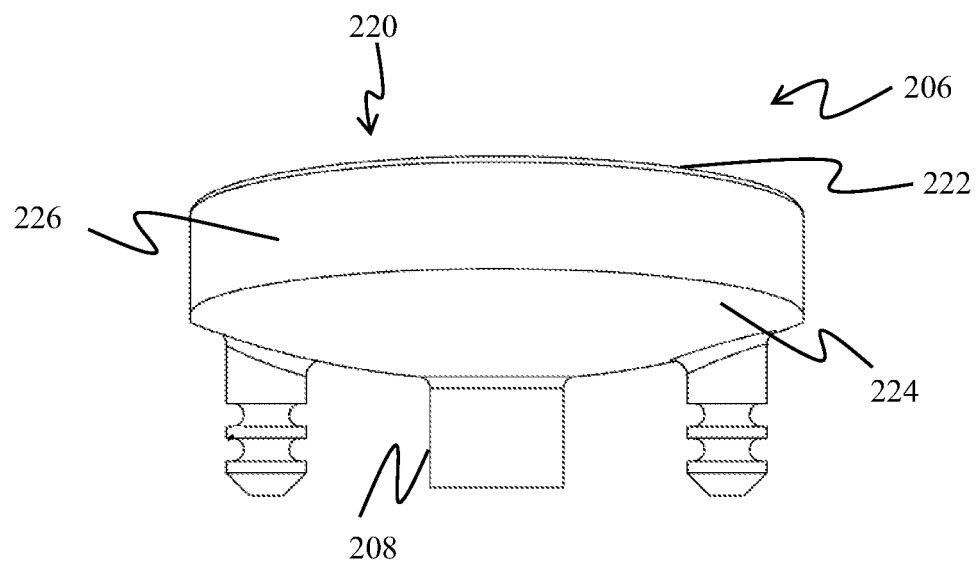
FIG. 3A is an isometric view of an articulating component.
Figure 3B:
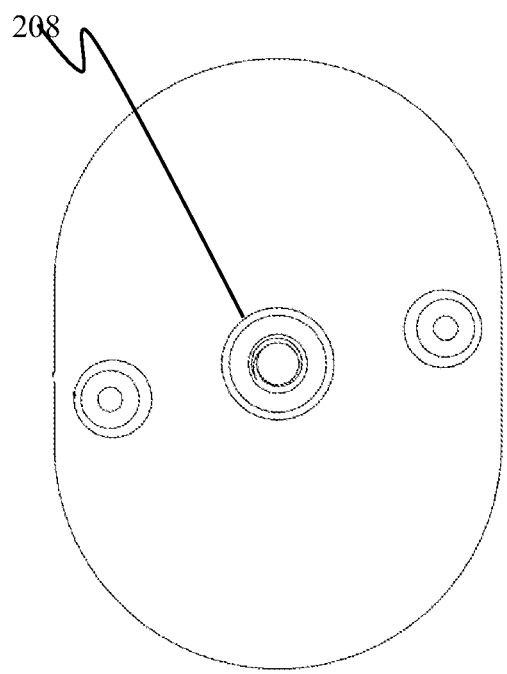
FIG. 3B is a bottom view of the articulating component of FIG. 3A.

Referring to FIGS. 3A-3B, an articulating component 206 may be engaged with the bone. A fixation means 208 may be provided in the articulating component 206 to enable fixing of a post. The articulating component 206 may include a body 220, an articulating surface 222 and a bone-facing surface 224. The body 220 may be shaped to mirror an anatomical shoulder. The articulating surface 222, which may also be referred to as a first surface, may be smooth or rough on a micro or macroscopic level. The articulating surface 222 may be semi-spherical or concave, and may be peripherally surrounded by a wall 226, which may also be referred to as a side portion. The wall 226 may extend between the articulating surface 222 and the bone-facing surface 224, where the bone-facing surface 224 is opposite to the articulating surface 222. When inserted, the bone-facing surface 224 may rest against the shoulder bone. The distal bone facing surface 224 may also be referred to as second surface which is opposite to the articulating surface 222. The post may be disposed below the second surface 224.

Figure 4A:
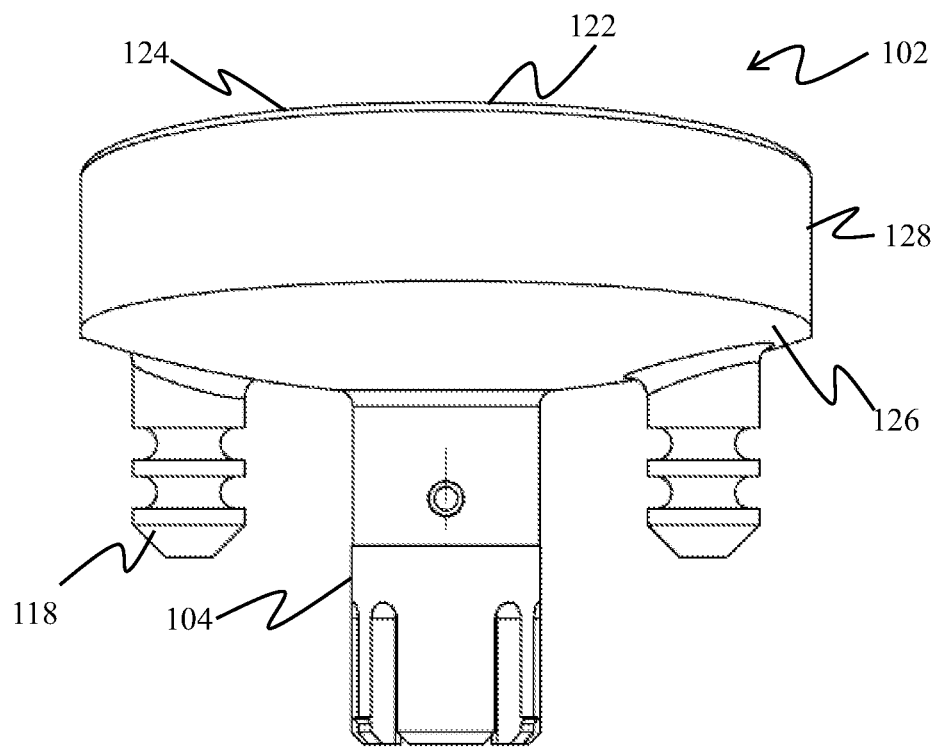
FIG. 4A is an isometric view of an articulating component with a post.
Figure 4B:
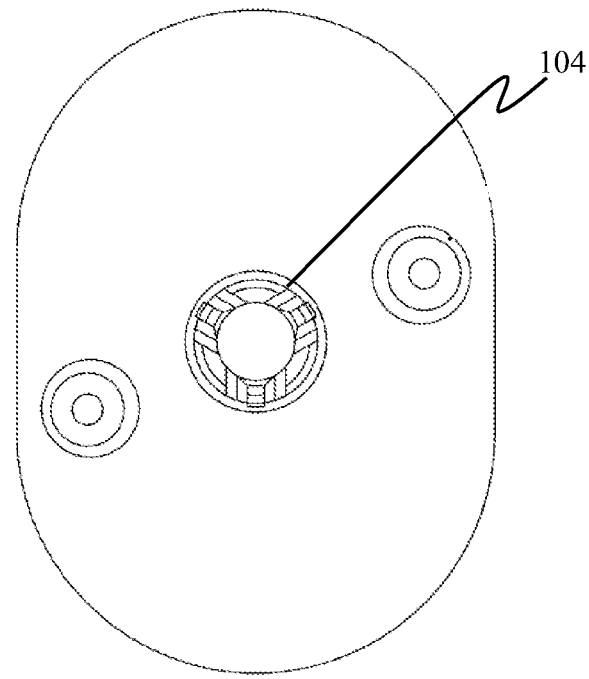
FIG. 4B is a bottom view of the articulating component with the post of FIG. 4A.

Referring to FIGS. 4A-4B, the articulating component 102 may include a post 104 which may be structurally integral to the articulating component 102. The articulating component 102 may include a body 122, an articulating surface 124 and a bone-facing surface 126. The body 122 may be shaped to mirror an anatomical shoulder. The articulating surface 124, which may also be referred to as a first surface, may be smooth or rough on a micro or macroscopic level. The articulating surface 124 may be semi-spherical or concave, and may be peripherally surrounded by a wall 128, which may also be referred to as a side portion. The wall 128 may extend between the articulating surface 124 and the bone-facing surface 126, where the bone-facing surface 126 is opposite to the articulating surface 124. When inserted, the bone-facing surface 126 may rest against the shoulder bone.

Figure 5A:
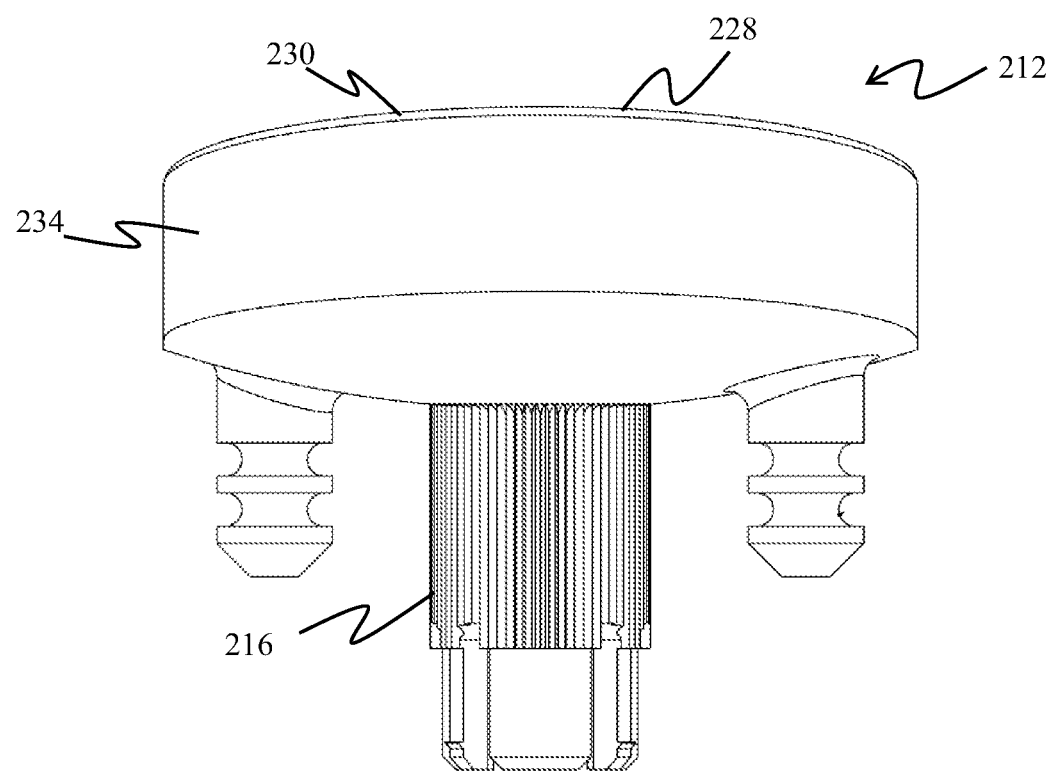
FIG. 5A is an isometric view of an articulating component with post spline.
Figure 5B:
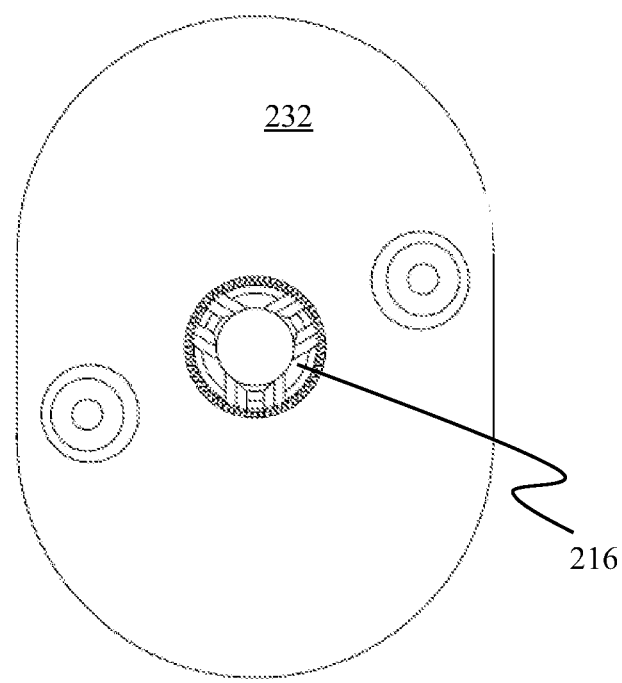
FIG. 5B is a bottom view of the articulating component with post spline of FIG. 5A.

Referring to FIGS. 5A-5B, an articulating component 212 may include a post 216 which may define splines 216 and may be structurally integral to the articulating component 212. The articulating component 212 may include a body 228, an articulating surface 230 and a bone-facing surface 232. The body 228 may be shaped to mirror an anatomical shoulder. The articulating surface 230, which may also be referred to as a first surface, may be smooth or rough on a micro or macroscopic level. The articulating surface 230 may be semi-spherical or concave, and may be peripherally surrounded by a wall 234, which may also be referred to as a side portion. The wall 234 may extend between the articulating surface 230 and the bone-facing surface 232, where the bone-facing surface 232 is opposite to the articulating surface 230. When inserted, the bone-facing surface 232 may rest against the shoulder bone.

Figure 6A:
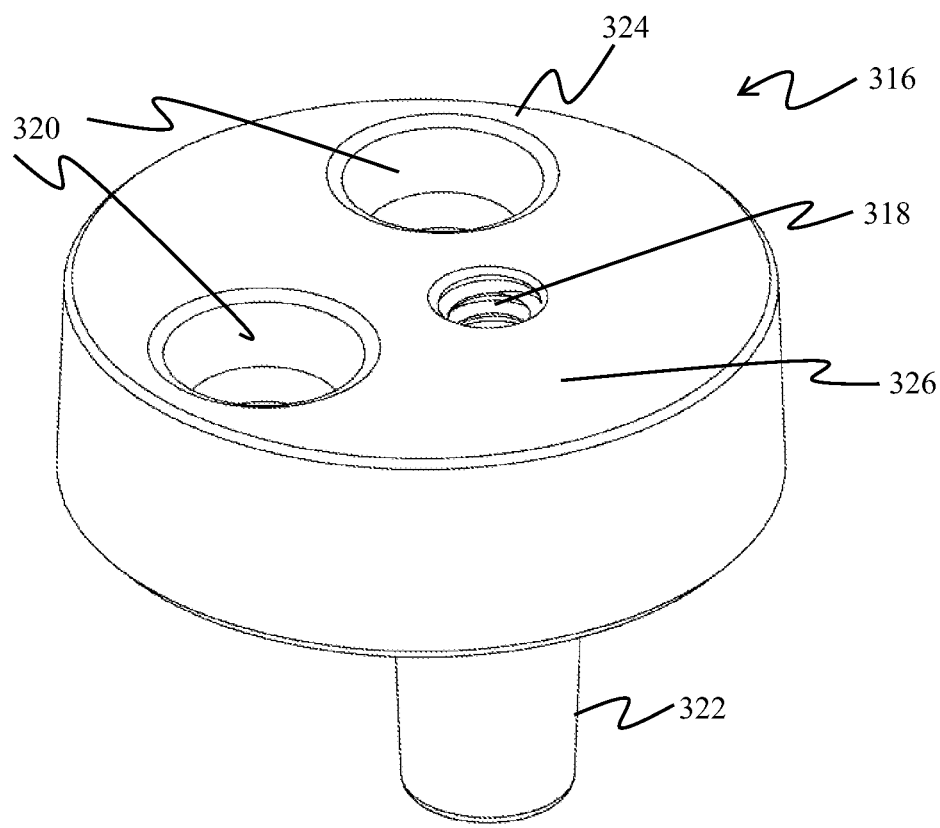
FIG. 6A is an isometric view of a metaglene component.
Figure 6B:
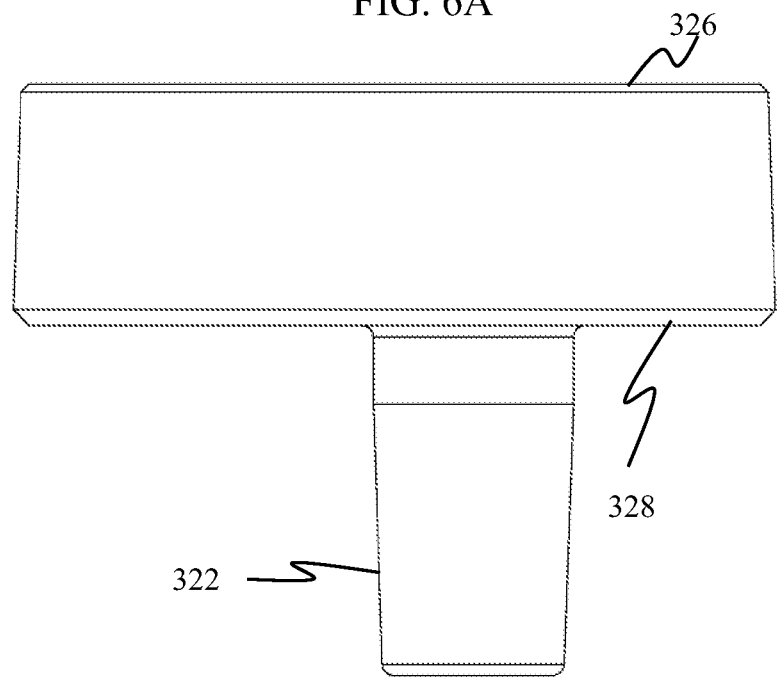
FIG. 6B is a side view of the metaglene component of FIG. 6A.

Referring to FIGS. 6A-6B, a metaglene component 316 may include a post 322 that extends substantially perpendicularly away from the distal surface 328 of the metaglene component 316. The metaglene component 316 may be formed separately from the glenosphere 202, and may be substantially disc-shaped or stoutly cylindrical.

Alternatively, the metaglene component 316 may be integrally formed with the body 203 of the glenosphere 202. The metaglene component 316 may otherwise be oval or polygonally shaped. Metaglene component 316 may further include a body 324, a first, glenosphere-facing surface 326 and a distal surface 328.

The metaglene component 316 may also include at least one metaglene hole(s) 320 that passes entirely through the body, and may be shaped to receive screws to fixate the metaglene component 316 to the bone. The metaglene component 316 may define an aperture 318 which may provide a place for securing an augment to the glenosphere.

The metaglene component 316 may also be attached to the glenosphere via a press or snap fit. After the metaglene component 316 is inserted into the recessed portion 218 of the glenosphere 202, the distal surface of the metaglene component 316 may sit flush with the bone facing surface 207 of the glenosphere 202.

The post 322 of the metaglene component 316 may be tapered from the proximal end to the distal end. The tapering of the post 322 may be such that it enables a friction fit with the tapered walls 414 a reception member 406 (illustrated in FIG. 10B).

Figure 7:
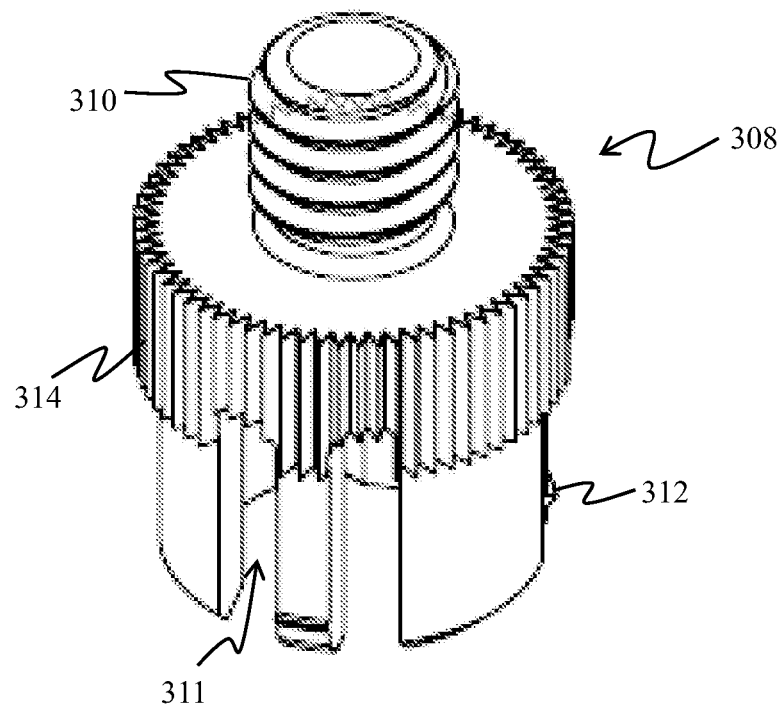
FIG. 7 is an isometric view of a post with splines.

Referring to FIG. 7, a post or connecting means 308 may include a threaded connecting means 310 which may be configured to connect to the fixation means 208 of the articulating component 206. Further, the post 308 may include at least one flexibility imparting means 311. The flexibility imparting means 311 may be a slot. In another embodiment, flexibility imparting means may be in the form of grooves or any other shape configured to impart flexibility to the post 308. The post 308 may define post splines 314 on its outer surface. The post splines 314 may be defined along the entire length or just a portion of the post 308. The post spline 314 engages with the reception member spline 414 provided on the inside surface of the reception member 406. The post 308 may further include a ratchet interface 312 to enable snap fitting of the post 308 into a ratchet interface 412 of the reception member 406.

Figure 8:
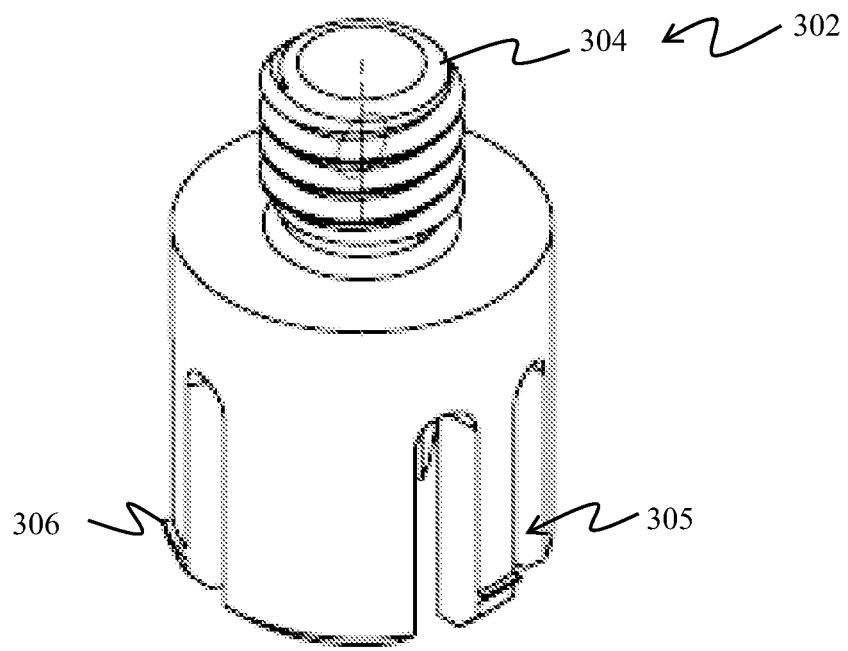
FIG. 8 is an isometric view of a post.

Referring to FIG. 8, a post or connecting means 302 may include a threaded connecting means 304 which may be configured to engage with the fixation means 208 of the articulating component 206. Further, the post 302 may include at least one flexibility imparting means 305. The flexibility imparting means 305 may be a slot. In another embodiment, flexibility imparting means 305 may be in the form of grooves or any other shape configured to impart flexibility to the post 302. The post 302 may include a ratchet interface 306 to enable snap fitting of the post 302 into a ratchet interface 404 (illustrated in FIG. 11C) of the reception member 108.

Figure 9:
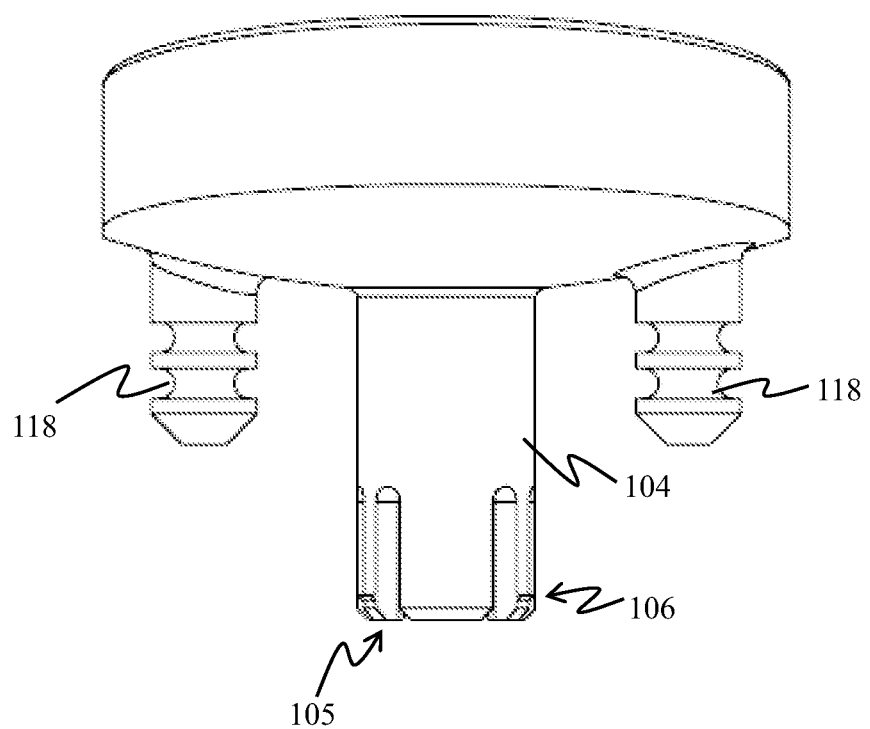
FIG. 9 is an isometric view of a post which may be structurally integral to the articulating component.

Referring to FIG. 9, a post or connecting means 104 may be used and be structurally integral with the articulating component 102. The post 104 may include at least one flexibility imparting means 105. The flexibility imparting means 105 may be a slot. In another embodiment, flexibility imparting means 105 may be in the form of grooves or any other shape configured to impart flexibility to the post 104.

The post 104 may include a ratchet interface 106 to enable snap fitting of the post 104 into a ratchet interface 404 of the reception member 108.

Figure 10:
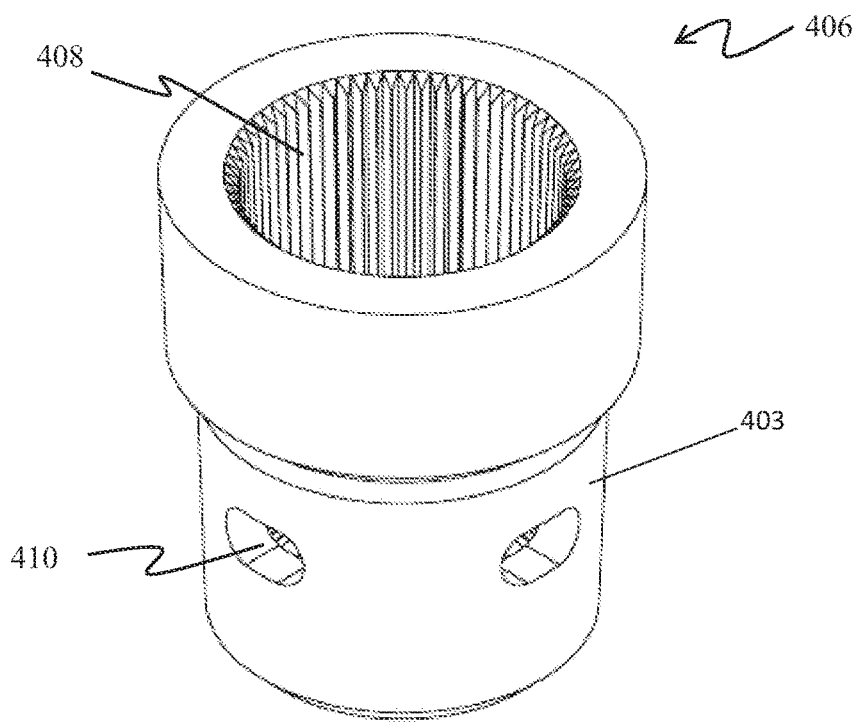
FIG. 10A is an isometric view of a reception member.
FIG. 10B is a cross-sectional view of the reception member of FIG. 10A.
Figure 10B:
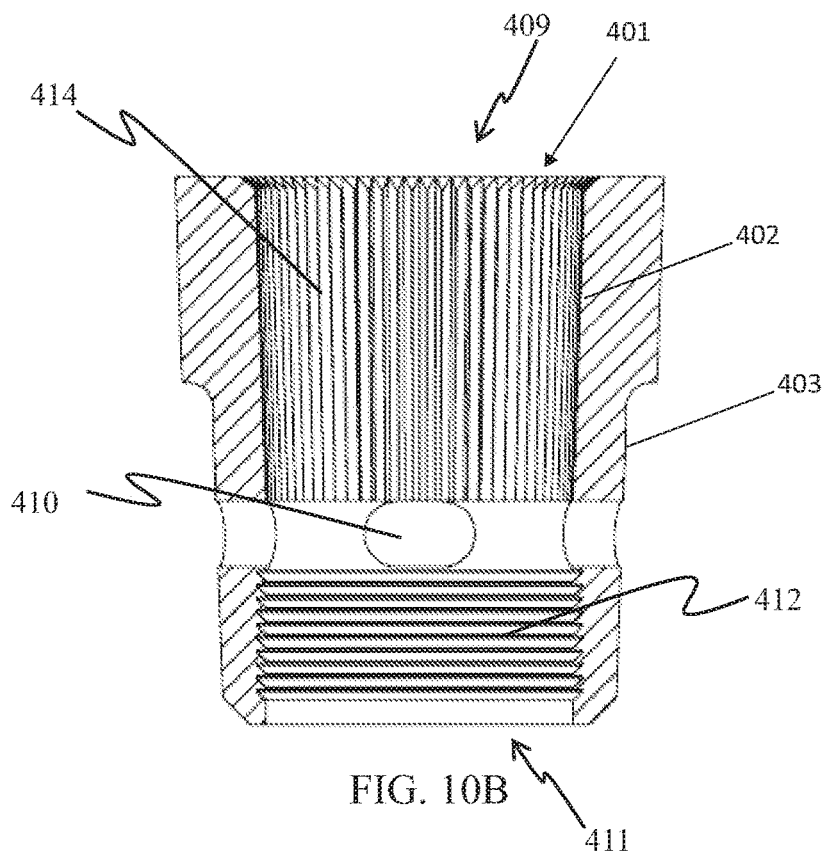

Referring to FIGS. 10A-10B a reception member or reception means 406 may comprise a proximal end 409 and a distal end 411. A bore 401 extends through the reception member 406 from the proximal end 409 to the distal end 411. The reception member 406 may further include at least one installation-extraction slot or through-hole or installation-extraction means 410 that extends from a reception member inner wall or inside surface 402 away from the bore 401 to an outside surface 403 of the reception member 406. Reception member splines 414 may be defined on the inner surface of the reception member 406 from the proximal end 409 towards the distal end 411. The reception member splines 414 may extend to the installation-extraction slot 410. The reception member splines 414 of the reception member 406 may be configured to receive the post splines 314 of the post 308. Upon reception of the post 308 with post splines 314 in the reception member splines 414, the rotation of the post 308 about a longitudinal axis of the post 308 may be restricted. The inside surface 407 of the reception member 406 may include the ratchet interface 412. The ratchet interface 412 of the reception member 406 may be configured to engage with the ratchet interface 312 of the post 308. A portion of the outer wall or outside surface 403 of the reception member 406 may be tapered. The outside surface 403 of the reception member 406 may define a step. The step may be such that it may engage with the step provided on the inside surface of the central ring 516 (illustrated in FIG. 14B) of the bone engaging member 110.

Figure 11A:
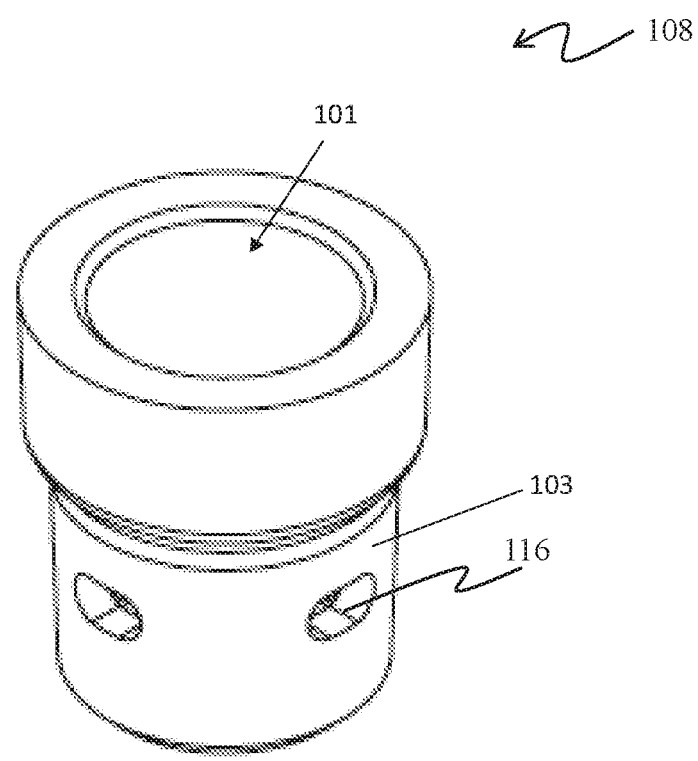
FIG. 11A is an isometric view of a reception member.
Figure 11:
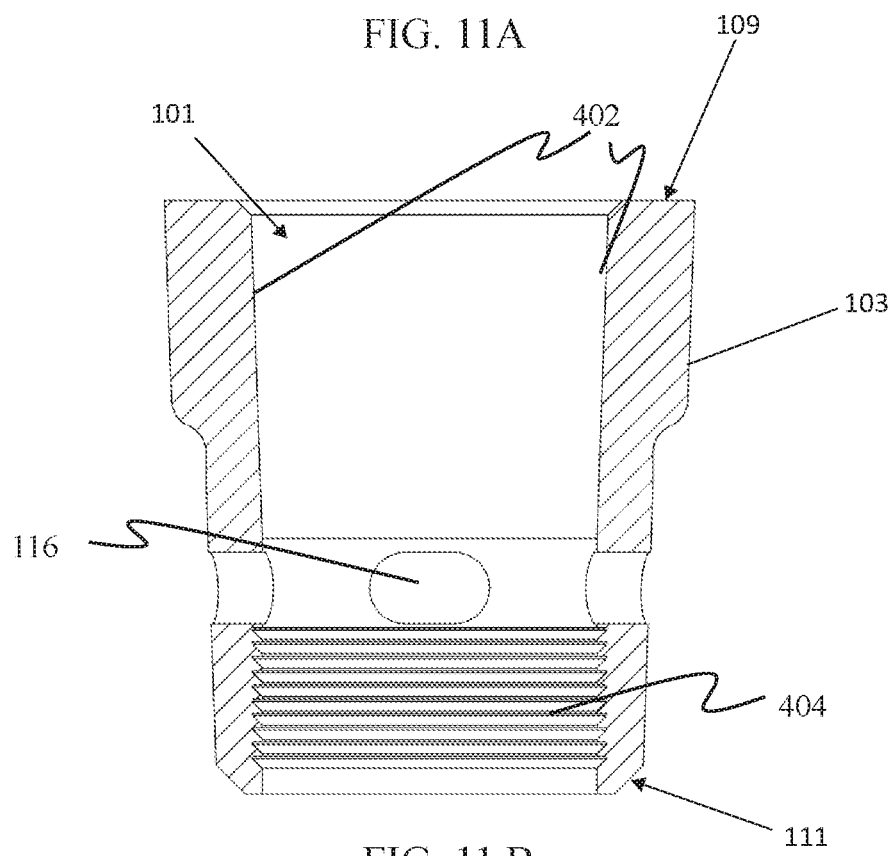
FIG. 11B is a cross-sectional view of the reception member of FIG. 11A.

Referring to FIGS. 11A-11B the reception member or reception means 108 may include a bore 101 that extends through the reception member 108 from the proximal end 109 to the distal end 111 and at least one installation-extraction slot or installation-extraction means 116 that extends from a reception member inner wall or inside surface 402 away from a bore 101 to an outside surface 103 of the reception member 108. The inside surface 402 of the reception member 108 may include the ratchet interface 404. The ratchet interface 404 of the reception member 108 may be configured to engage with the ratchet interface 306 of the post 302, resulting in snap fitting of the post 302 with the reception member 108. A portion of the outer wall or outside surface 103 of the reception member 108 may be tapered. The inner walls 402 may be tapered from the proximal end 109 towards the distal end 111 up to the installation-extraction slot 116 of the reception member 108. A portion of the inside surface 402 of the reception member 108 may be tapered. The tapering of the inside surface 402 of the reception member 108 may facilitate interference fitting of the post 302 with the reception member 108.

Figure 12A:
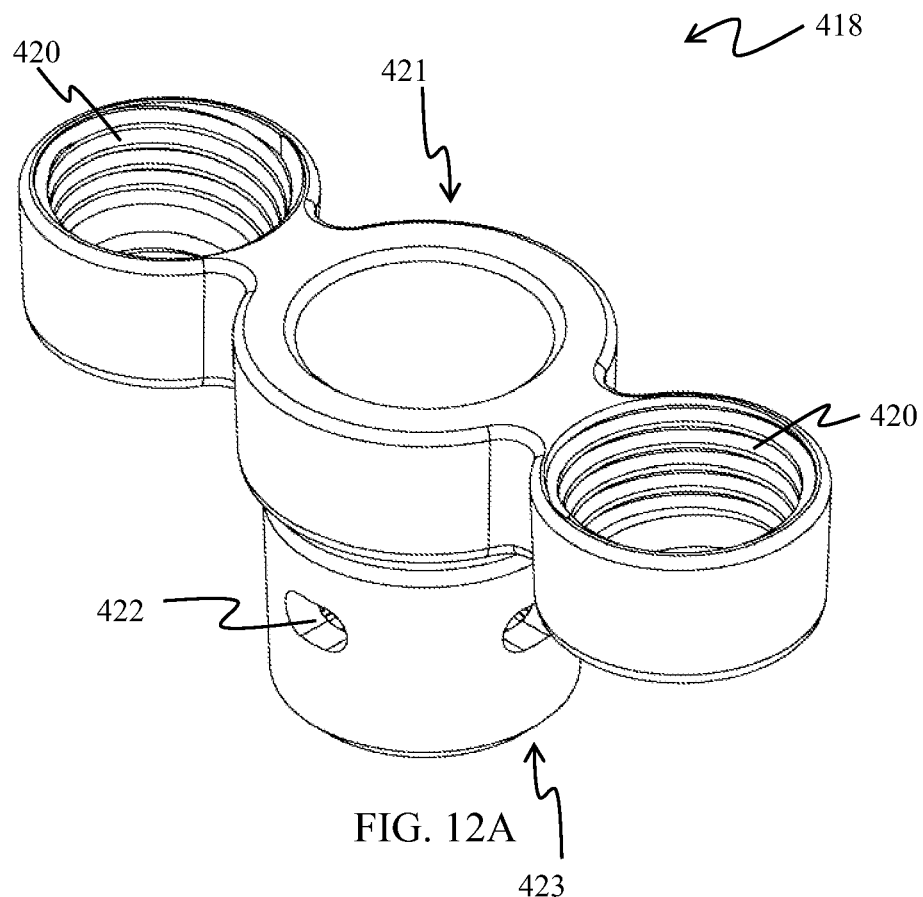
FIG. 12A is an isometric view of a reception member.
Figure 12B:
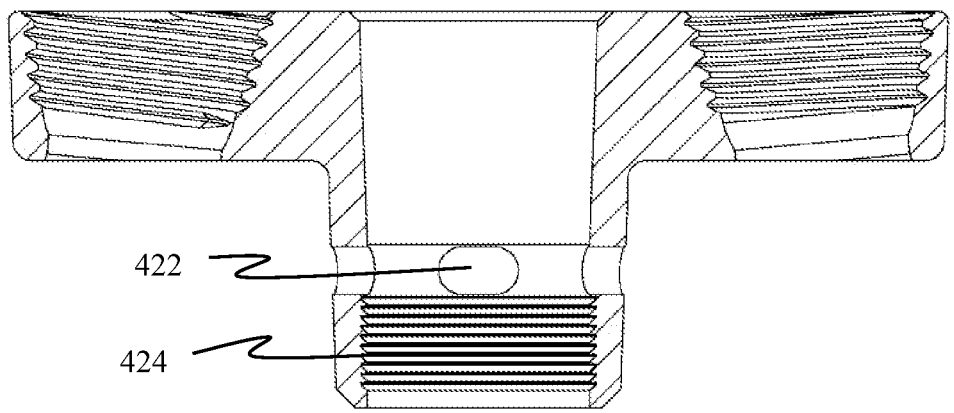
FIG. 12B is a cross-sectional view of the reception member of FIG. 12A.

Referring to FIGS. 12A-12B the reception member or reception means 418 may include at least one bore 420 at the proximal end 421. The bores 420 may facilitate anchoring of the reception member 418 to the bone. The reception member 418 further comprises at least one installation-extraction slot or installation-extraction means 422. The inside surface of the reception member 418 may include a ratchet interface 424. The ratchet interface 424 of the reception member 418 may be configured to engage with the ratchet interface 306 of the post 302, resulting in snap fitting of the post 302 with the reception member 418. A portion of the outer wall of the reception member 418 may be tapered. The inner walls of the reception member 418 may be tapered from the proximal end 421 towards the distal end 423 up to the installation-extraction slot 422 of the reception member 418. The inside surface of the reception member 418 may be tapered. The tapering of the inside surface of the reception member 418 may enable interference fitting of the post 302 with the reception member 418.

Figure 13A:
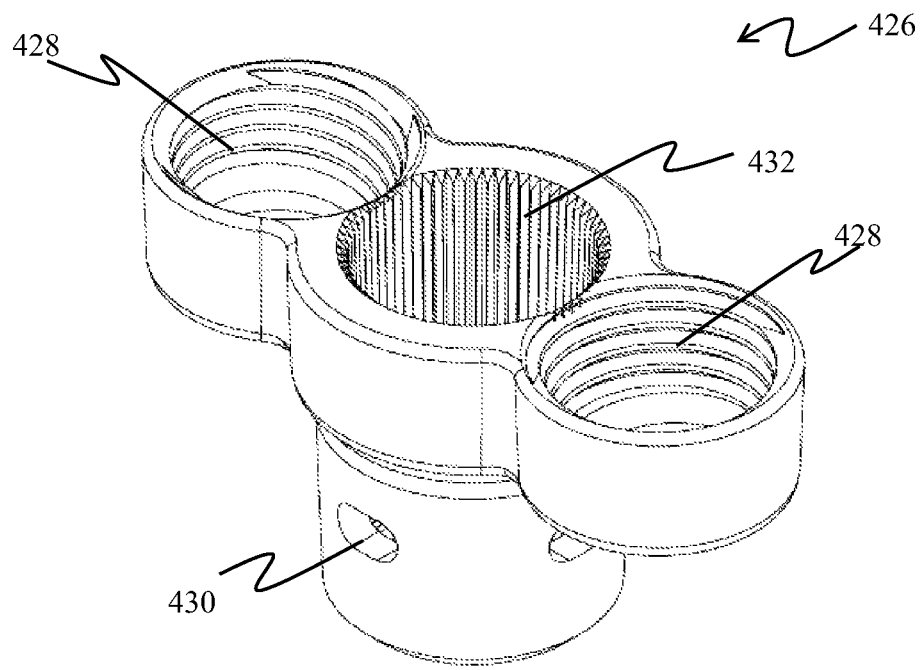
FIG. 13A is an isometric view of a reception member.
Figure 13B:
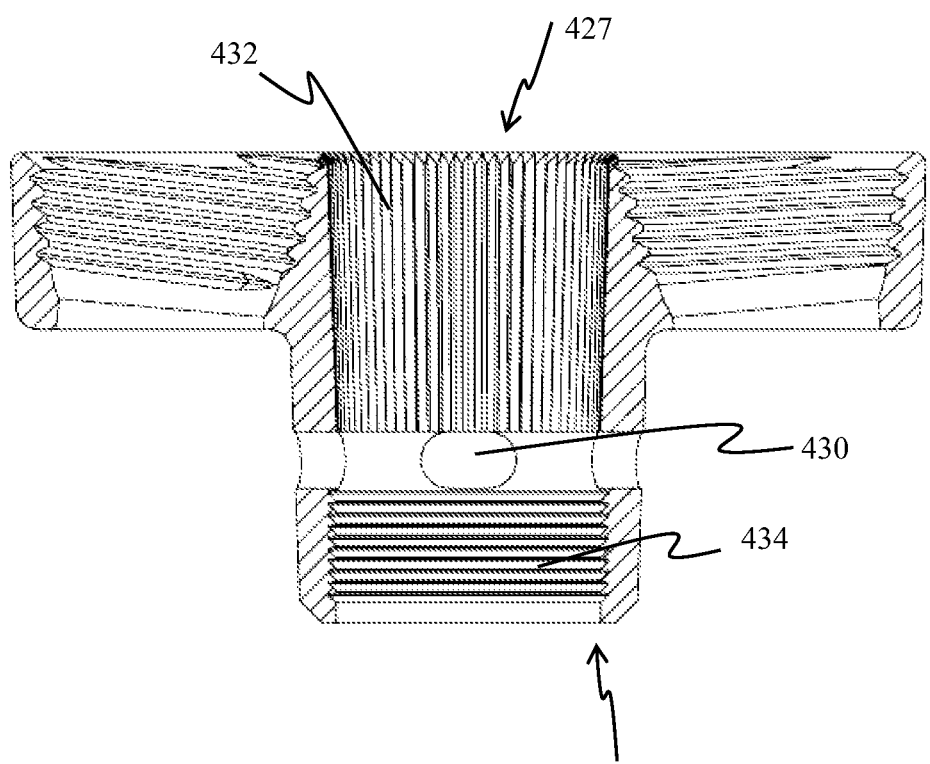
FIG. 13B is a cross-sectional view of the reception member of FIG. 13A.

Referring to FIGS. 13A-13B a reception member or reception means 426 may comprise the proximal end 427 and the distal end 429. The reception member 426 may further comprise at least one bore 428 at the proximal end 427. The bores 428 may facilitate anchoring of the reception member 426 to the bone. The reception member 426 further comprises at least one installation-extraction slot or installation-extraction means 430. Reception member splines 432 may be defined on the inside surface of the reception member 426 from the proximal end 427 towards the distal end 429. The reception member splines 432 may extend to the installation-extraction slot 430. The reception member splines 432 may be configured to receive the post splines 314 of the post 308. Upon reception of the post 308 with post splines 314 in the reception member splines 432, the rotation of the post 308 about a longitudinal axis of the post 308 is restricted. The inside surface of the reception member 426 may include a ratchet interface 424. The ratchet interface 434 of the reception member 426 may be configured to engage with the ratchet interface 312 of the post 308, resulting in snap fitting of the post 308 with the reception member 426. A portion of the outer wall of the reception member 426 may be tapered. The inner walls of the reception member 426 may be tapered from the proximal end 427 towards the distal end 429 up to the installation-extraction slot 430 of the reception member 426.

Figure 14A:
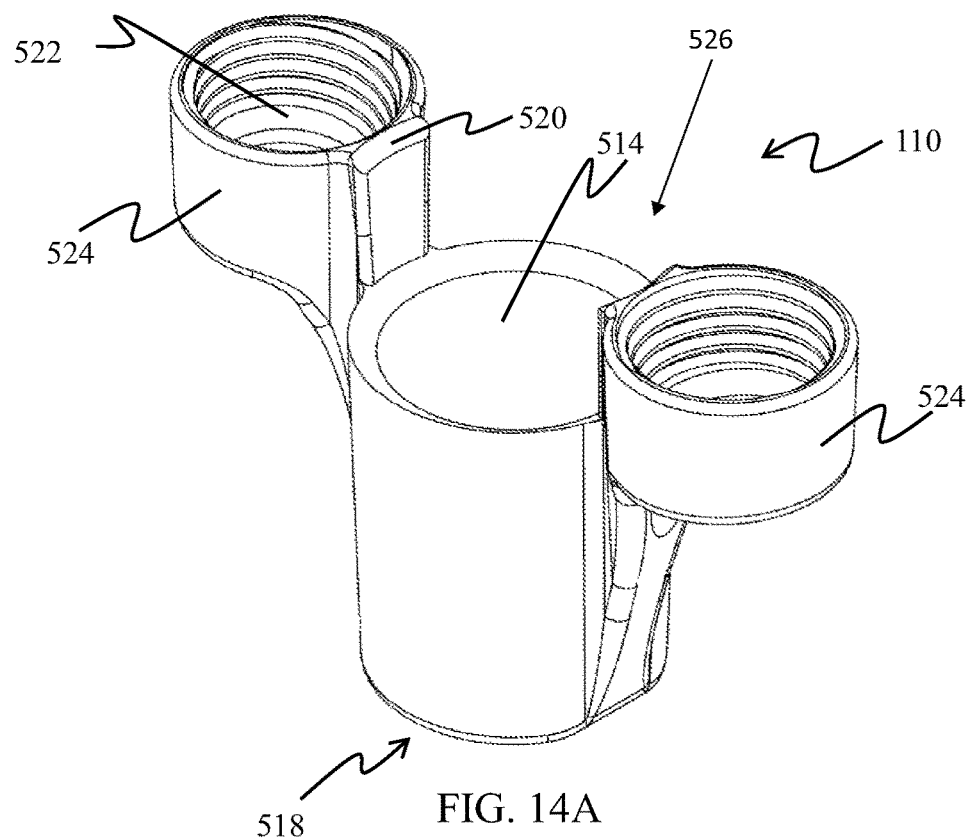
FIG. 14A is an isometric view of a bone engaging member.
Figure 14B:
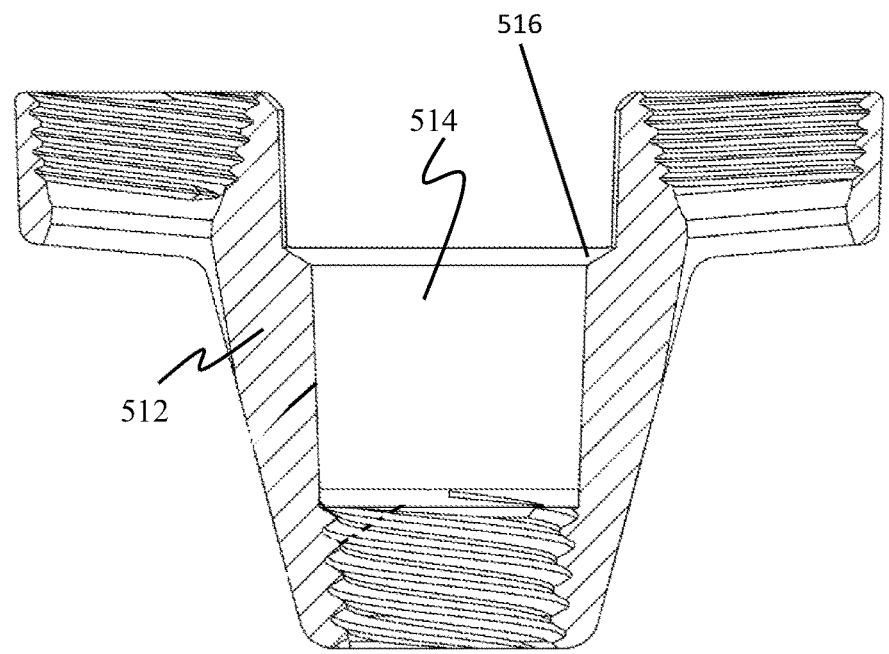
FIG. 14B is a cross-sectional view of the bone engaging member of FIG. 14A.

Referring to FIGS. 14A-14B, the bone engaging member 110 may include a bore 514, which may be a central bore, extending at least partially through the body or central ring 516 in a longitudinal direction and may extend entirely through the central ring 516. The bone engaging member 110 includes a distal end 518 and may include two arms 520 extending from the central ring 516. The arms 520 may be integral to the body 516, or may be separately formed. The bone engaging member 110 include a proximal end 526 and a distal end 518 of the bone engaging member 110. Portions of the arms 520 extend proximally from the central ring 516 giving the bone engaging member 110 a V or U-shaped configuration for the bone engaging member 110. The extension of the arms 520 proximally may be substantially parallel and substantially the same length, wherein the arms are coplanar; however the arms may differ in length slightly as well which may give the bone engaging member 110 a J-shape, wherein the arms are not coplanar. The extension of the arms 520 may be collinear and the arms 520 may prove to be mirror images if a cross section is taken of the bone engaging member 110. The portion of the arms 520 toward the central ring 516 may cylindrically curved around the central ring 516 with the same degree of curvature as the central ring 516.

The arm 520 may include an opening or bore 522 defined by a wall 524, which may be an arm ring, which may be cylindrical in shape, at the end of the arm 520. Bores 522 may also be referred to as lateral passages. The arm ring 524 may protrude from the arm 520 in substantially the same direction as the arm 520 extending from the central ring 516. The opening 522 may extend entirely through the arm ring 524 substantially parallel with the central bore 514. The opening 522 is substantially circular in cross section and configured to receive the screw 120. The opening 522 may be a double conical shape with the narrowest point seated toward the middle of the opening 114, the shape expanding outward toward either end of opening 522. The opening 522 may slidably or threadably receive the screws 120.

The bore 514 defines threading on an inside surface 502 at the distal end 518. The bore 514 is configured to receive the anchor 114. The threading provided on the inside wall 502 at the distal end 518 of the bore 514 is configured to mate with the threading provided at the proximal end of the anchor 114. This configuration enables anchoring of the bone engaging member 110 with the bone, wherein the anchor 114 is held within the bone engaging member 110. The inside surface 502 of the central ring 516 may be tapered from the proximal end 526 towards the distal end 518 of the bone engaging member 110. The tapering of the inside wall 502 may be complimentary to the tapering of the outside wall of the reception member or reception means 108. The inside surface of the central ring 516 may define at least one step. The step of the bone engaging member 110 may be such that it restricts the movement of the reception member 108 towards the distal end of the bone engaging member 110.

Figure 15:
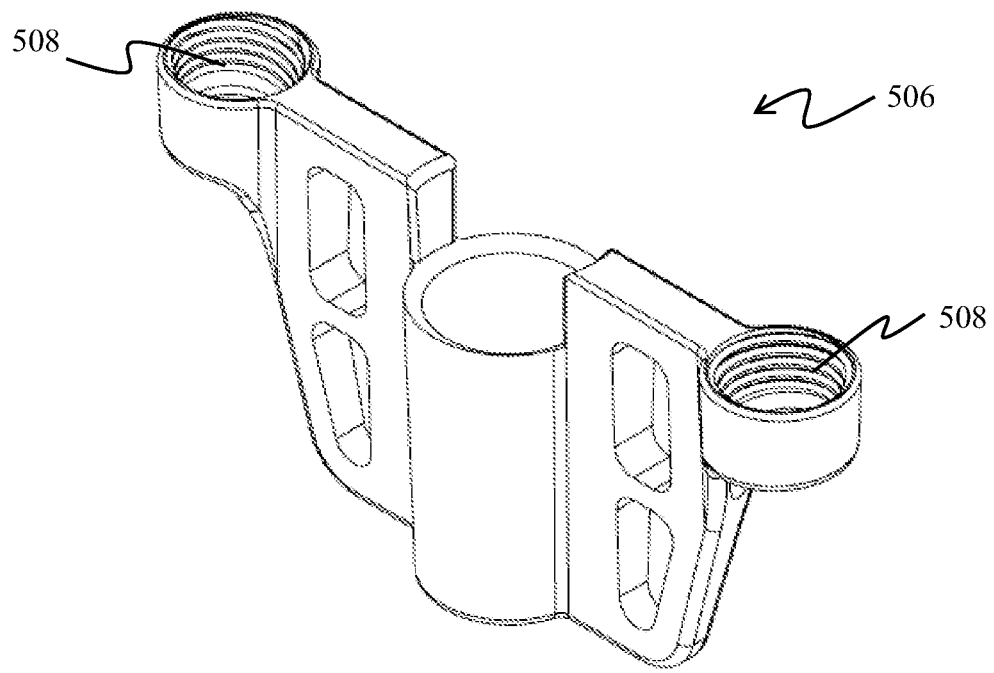
FIG. 15A is an isometric view of a bone engaging member.
FIG. 15B is a cross-sectional view of the bone engaging member of FIG. 15A.
Figure 15:
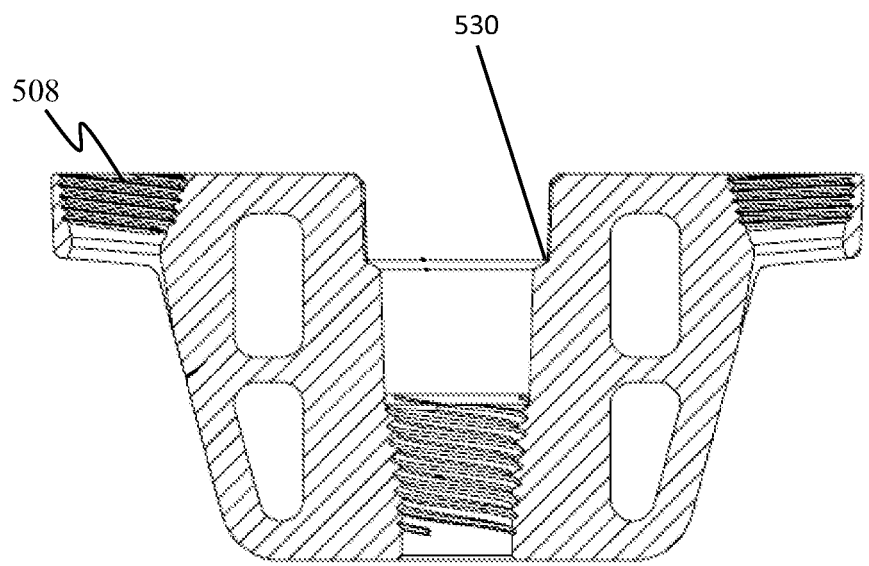

FIGS. 15A-15B illustrate an isometric view and cross-sectional view respectively of an alternate embodiment of a bone engaging member 506. Arms 508 connect a central ring 530 to bore 514 (labeled in FIGS. 14A and 14B). The arms 508 define slots. The slots may facilitate growth of bone through the slots, which may result in firm fixation of the bone engaging member 506 with the bone.

Figure 16:
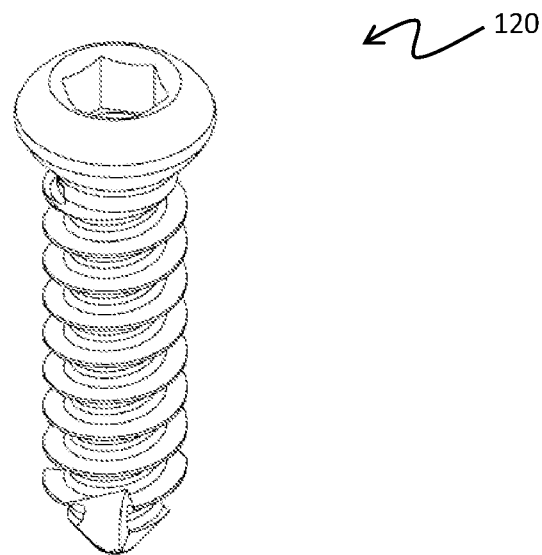
FIG. 16 is an isometric view of a screw.

FIG. 16 illustrates a screw 120 which may be inserted into the bores 112 to engage the bone engaging member 110 to the bone.

Figure 17:
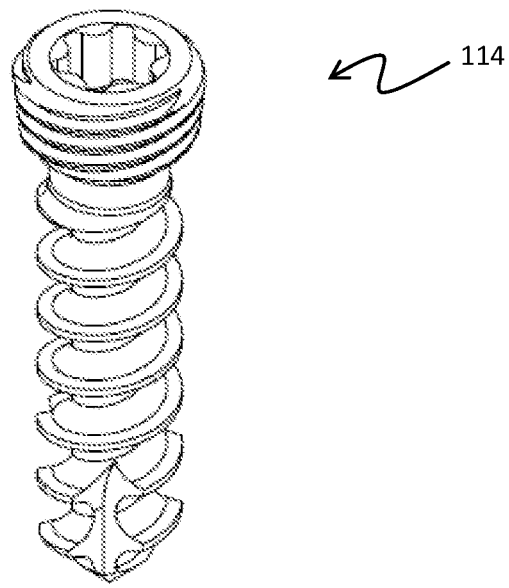
FIG. 17 is an isometric view of an anchor.
Figure 18A:
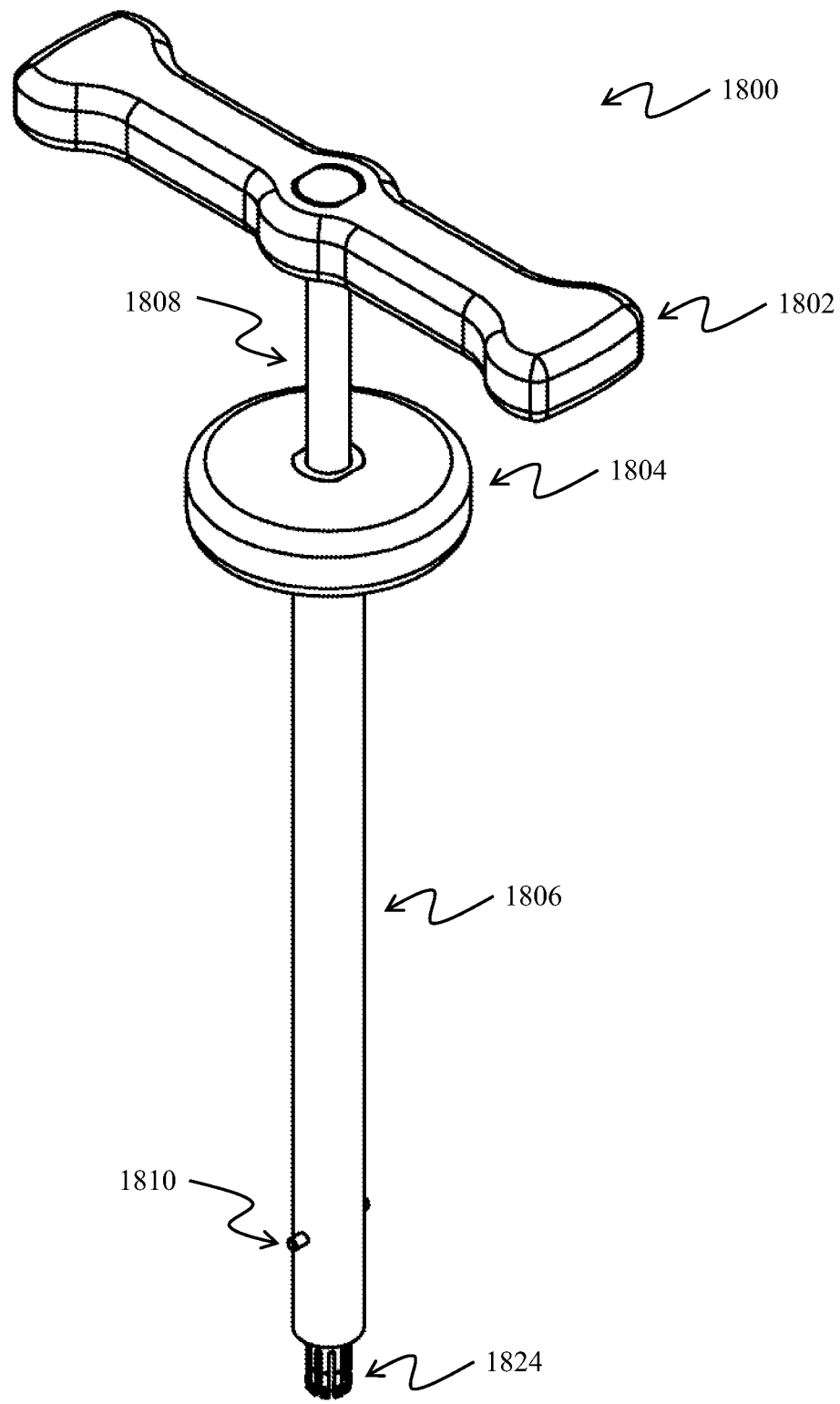
FIG. 18A is an isometric view of an instrument for inserting or extracting a reception member.
Figure 18:
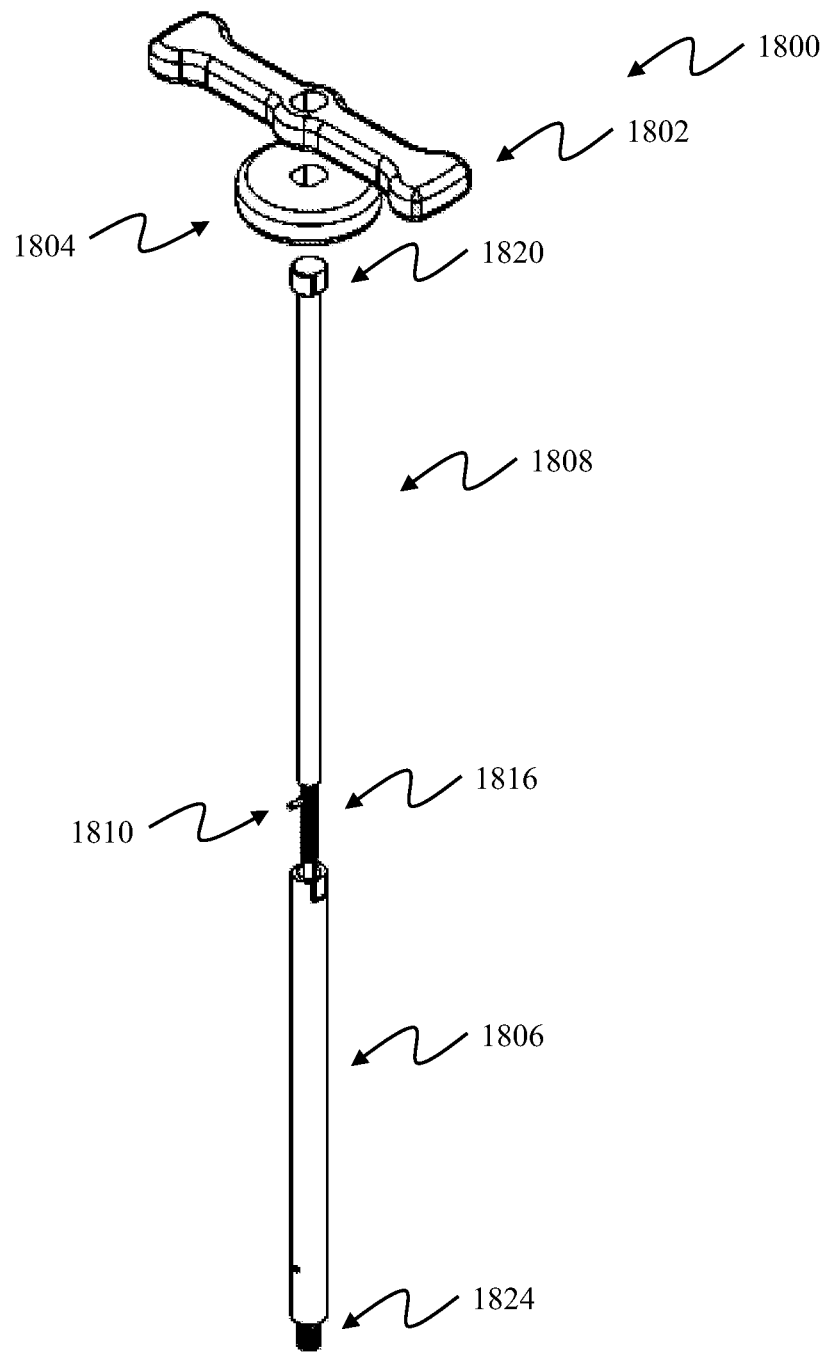
FIG. 18B is an exploded view of the instrument of FIG. 18A.
FIG. 18C is a cross-sectional view of the instrument of FIG. 18A.
FIG. 18D is close up of prongs of the instrument of FIG. 18A.
FIG. 18E is close up of another prong configuration.
Figure 18:
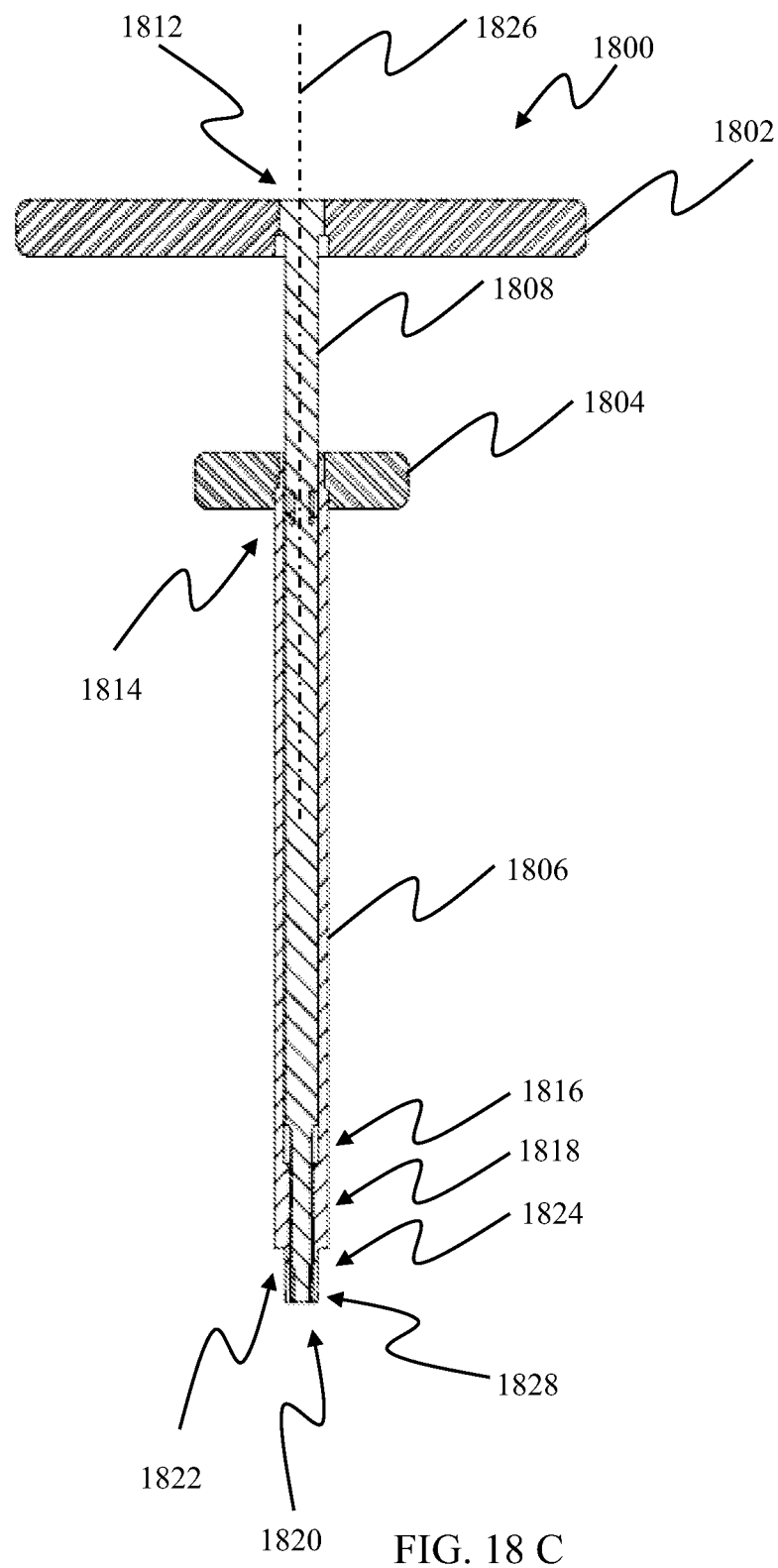
Figure 18:
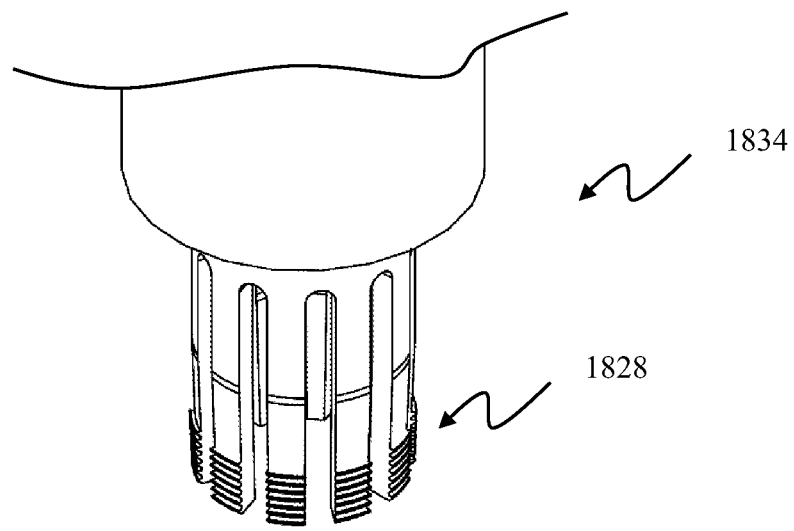
Figure 18:
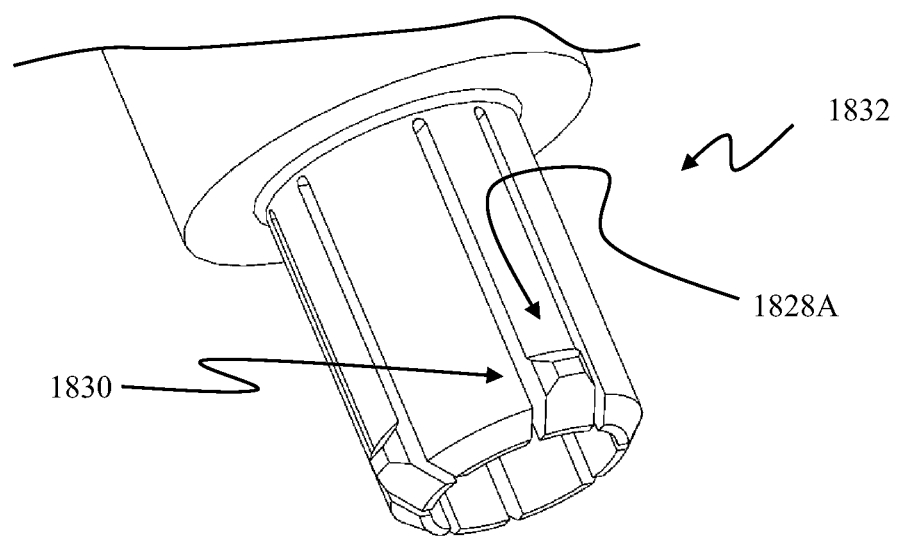

FIG. 17 illustrates an anchor 114 which may be inserted into the bore 514 of the bone engaging member 110 to anchor the bone engaging member 110 to the bone.

Referring to FIGS. 18A-18E, an instrument 1800 may be used for inserting or extracting a reception member, or reception means or anterior posterior component. The instrument 1800 may include a handle 1802, a grip member 1804, a housing 1806, a shaft 1808 and a pin 1810.

A proximal end 1814 of the housing 1806 is engaged with the grip member 1804. The shaft 1808 may be received by the housing 1806, such that a proximal end 1812 of the shaft 1808 protrudes out of the proximal end 1814 of the housing 1806, and extends through the grip) member 1804. The proximal end 1812 of the shaft 1808 may be engaged with the handle 1802. The pin 1810 may be received by the housing 1806 and the shaft 1808 such that rotation of the shaft 1808 relative to the housing 1806 is prevented.

The shaft 1808 may include a threaded portion 1816, and the housing 1806 may also define a threaded portion 1818. The threaded portion 1816 of the shaft 1808 may mate with the threaded portion 1818 of the housing 1806. Application of torsion force to the handle 1802 may result in rotation of the shaft 1808. The pin 1810 may be disengaged when such rotation is desired. Rotation of the shaft 1808 may result in the shaft 1808 extending out of the housing 1806, such that a distal end 1820 of the shaft 1808 moves away from a distal end 1822 of the housing 1806. An operator can hold the grip member 1804 in one hand, while the operator applies torsion force to the handle 1802 using the other hand. Application of torsion force to the handle 1802 when the pin 1810 is engaged may result in rotation of the entire instrument 1800.

The housing 1806 may include one or more prongs 1824 towards the distal end 1822 of the housing 1806. The prongs 1824 may be flexible such that the prongs 1824 may be pushed towards a central axis 1826 of the shaft 1808 when a force pushing the prongs 1824 is applied.

The prongs 1824 may define a ratchet interface 1828 and 1828A. Further, at least a portion of the ratchet interface 1828A may define at least one chamfered surface 1830, such that the chamfered surface 1830 enables the ratchet interface 1828 to be disengaged from a corresponding ratchet interface defined in, for example, the reception member.

The instrument 1800 may be used for inserting a reception member such as the reception member 108. The pin 1810 may be engaged through the housing 1806 and the shaft 1808, thereby restricting relative movement between the housing 1806 and the shaft 1808. The reception member may be engaged to the prong 1824. The ratchet interface 1828 may be engaged with a corresponding interface defined in the reception member. For example, the ratchet interface 1828 may be engaged in the installation-extraction slot 116 defined in the reception member 108. Subsequently, the reception member may be inserted into the bone engaging member.

Once the reception member is aligned and in position within the bone engaging member, a relatively permanent fixation via taper-locking between the reception member and bone engaging member may be accomplished by impaction, for example by use of one or more strikes of a mallet to the handle 1802. Once the reception member is engaged, torsion force is applied to the handle 1802, which results in rotation of the housing 1802. At this point, it may be worthy to note that, the chamfered surface 1830 enable the prongs 1824 to disengage from the installation-extraction slot 116 defined in the reception member 108. Once the prongs 1824 are disengaged, the instrument may be pulled out.

The instrument 1800 may be used for extracting the reception member out of the bone engaging member. The pin 1810 may not be engaged through the housing 1806 and the shaft 1808, thereby allowing the shaft 1808 to rotate relative to the housing 1806. The instrument 1800 may be inserted into the reception member. Upon insertion, the prongs 1824 may engage a slot defined in the reception member. Torsion force may be applied to the handle 1802, which results in rotation of the shaft 1808. Rotation of the shaft 1808 may result in the shaft 1808 extending out of the housing 1806, and eventually extends beyond the prongs 1824. The distal end 1820 of the shaft 1808 may be eventually obstructed, for example by the head of an anchor that may be used to engage the bone engaging member to the bone. Further application of torsion force to the handle 1802, which may force the shaft 1808 to extend further down, may result in pushing of the reception member out of the bone engaging member. Rotation of the handle 1802 may be stopped once the reception member is disengaged from the bone engaging member. The reception member, which may still be engaged to the prongs 1824, may be pulled out completely.

Prongs 1832 may be provided, which may have a ratchet interface 1834, configured to interface with a corresponding interface provided in the reception member.

The prongs 1832 may be configured to engage a distal end of the reception member, which may enable insertion and/or extraction of the reception member.

The components disclosed herein may be made from metals, polymers, ceramics, glasses, composite materials, biological materials or tissues, insulators, conductors, semi-conductors, or other biocompatible or non-biocompatible materials. Different materials may be used for individual components. Different materials may be combined in a single component.

It should be understood that the present systems, kits, apparatuses, and methods are not intended to be limited to the particular forms disclosed. Rather, they are to cover all combinations, modifications, equivalents, and alternatives falling within the scope of the claims.

The claims are not to be interpreted as including means-plus- or step-plus-function limitations, unless such a limitation is explicitly recited in a given claim using the phrase(s) "means for" or "step for," respectively.

The term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" an any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

The present invention may be embodied in other specific forms without departing from its spirit or essential characteristics. It is appreciated that various features of the above described examples and embodiments may be mixed and matched to form a variety of other combinations and alternatives. It is also appreciated that this system should not be limited simply to glenoid and/or scapular restoration. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A system, comprising:
   an articulating component comprising an articulating surface and a second surface opposite the articulating surface;
   a post disposed below the second surface;
   a reception member configured to receive the post; and
   a bone engaging member configured to be embedded in a bone, wherein the bone engaging member includes a bore that is configured to receive an anchor, the anchor being configured to couple the bone engaging member to the bone, wherein the bone engaging member is configured to receive the reception member in the bore above the anchor;
   wherein the reception member comprises a bore extending from a proximal end to a distal end of the reception member, a reception member inside surface, wherein the reception member inside surface faces the post when the post is received by the reception member, and wherein the reception member comprises at least one installation-extraction through-hole, wherein the installation-extraction through-hole extends from the reception member inside surface away from the bore to an outside surface of the reception member, wherein the outside surface faces the bone engaging member;

at least a first portion of the reception member inside surface defines a tapered configuration; and the reception member inside surface comprises at least one ratchet interface.

2. The system of claim 1, wherein at least a portion of the post defines a tapered configuration, wherein the portion of the post which defines the tapered configuration is configured to interface with the first portion of the reception member inside surface.

3. The system of claim 1, wherein the post comprises a ratchet interface, wherein the ratchet interface of the post engages with the ratchet interface of the reception member such that movement of the post along a longitudinal axis of the post away from the bone engaging member is generally prevented once the post is engaged with the reception member.

4. The system of claim 3, wherein the post defines at least one slot such that the ratchet interface of the post is operable to be pushed towards the center of the post upon application of a force which pushes the ratchet interface of the post towards a center of the post.

5. The system of claim 1, wherein,
the reception member inside surface defines at least one reception member spline;
the post comprises an outside surface, wherein the outside surface of the post defines at least one post spline; and
the post spline engages with the reception member spline such that once the post is engaged with the reception member rotation of the post about a longitudinal axis of the post is restricted.

6. The system of claim 1, wherein,
a portion of the outside surface of the reception member tapers towards a distal end of the reception member;
the bone engaging member comprises a bone engaging member inside surface, wherein a portion of the bone engaging member inside surface tapers towards a distal end of the bone engaging member; and
the portion of the outside surface of the reception member interfaces with the portion of the bone engaging member inside surface, thereby providing at least an interference fit between the reception member and the bone engaging member.

7. The system of claim 1, wherein the post is engaged to the articulating component using a threaded configuration.

8. The system of claim 1, wherein,
the outside surface of the reception members defines at least one step;
the bone engaging member comprises an inside surface defining at least one step; and
the step of the reception member interfaces with the step of the bone engaging member such that movement of the reception member towards a distal end of the bone engaging member is limited.

9. The system of claim 1, wherein,
the first portion of the reception member is closer to the proximal end of the reception member; and
the ratchet interface of the reception member is closer to the distal end of the reception member.

10. A method comprising:
embedding a bone engaging member in a bone wherein the bone engaging member includes a bore that is configured to receive and to engage an anchor;
engaging the anchor with the bone engaging member to couple the bone engaging member to the bone;
engaging a reception member in the bore of the bone engaging member above the anchor, wherein the reception member comprises a bore extending from a proximal end to a distal end of the reception member, a reception member inside surface comprising a first portion defining a tapered configuration, and the reception member inside surface comprises at least one ratchet interface, and wherein the reception member comprises at least one installation-extraction through-hole, wherein the installation-extraction through-hole extends from the reception member inside surface away from the bore to an outside surface of the reception member, wherein the outside surface faces the bone engaging member;
engaging a post with the reception member, wherein at least one of the tapered configuration and the ratchet interface interfaces with a corresponding feature provided in the post; and
engaging an articulating component with the reception member, wherein the post connects the articulating component with the reception member.

11. The method of claim 10, wherein engaging the post with the reception member comprises engaging a portion of the post defining a tapered configuration with the first portion of the reception member inside surface.

12. The method of claim 10, wherein engaging the post with the reception member comprises engaging a ratchet interface provided in the post with the ratchet interface of the reception member.

13. The method of claim 10, further comprising one of (a) installing the reception member into the bone engaging member and (b) extracting the reception member out of the bone engaging member by engaging an instrument with the at least one installation-extraction through-hole.

14. The method of claim 10, further comprising restricting rotation of the post about a longitudinal axis of the post by engaging at least one reception member spline defined by the reception member inside surface with at least one post spline defined by an outside surface of the post.

15. The method of claim 10, further comprising enabling the ratchet interface of the post to be pushed towards the center of the post upon application of a force which pushes the ratchet interface of the post towards a center of the post.

16. A system comprising:
a bone engaging means configured to be embedded in a bone, wherein the bone engaging means includes a bore that is configured to receive an anchor, the anchor being configured to couple the bone engaging means to the bone;
a reception means comprising a bore extending from a proximal end to a distal end of the reception member, an inside surface, wherein the inside surface is configured to provide at least one of an interference fit and a snap fit, wherein the reception means is configured to be received in the bore of the bone engaging means above the anchor, and wherein the reception means comprises at least one installation-extraction through-hole, wherein the installation-extraction through-hole extends from the reception means inside surface and extends away from the bore to an outside surface of the reception means, wherein the outside surface faces the bone engaging means;

a connecting means configured to establish at least one of the interference fit and the snap fit with the reception means; and an articulating means configured to be engaged with the reception member using at least the connecting means.

17. The system of claim 16, wherein each of the connecting means and the reception means comprises a rotation prevention means configured to restrict rotation of the connecting means about a longitudinal axis of the connecting means.

18. The system of claim 16, wherein the connecting means comprises a flexibility imparting means configured to enable at least a part of the connecting means, which is configured to establish the snap fit, to be flexible.

19. The system of claim 16, wherein the installation-extraction through-hole is configured to enable installation of the reception means into the bone engaging means or extraction of the reception means out of the bone engaging means.

* * * * *